United States Patent [19]

Huff et al.

[11] Patent Number: 4,690,928

[45] Date of Patent: Sep. 1, 1987

[54] SUBSTITUTED HEXAHYDRO ARYLQUINOLIZINES AS $\alpha_2$ BLOCKERS

[75] Inventors: Joel R. Huff, Lederach; Joseph P. Vacca, Telford; John J. Baldwin, Gwynedd Valley, all of Pa.

[73] Assignee: Merck & Co., Inc., Rahway, N.J.

[21] Appl. No.: 885,511

[22] Filed: Jul. 14, 1986

Related U.S. Application Data

[63] Continuation-in-part of Ser. No. 755,863, Jul. 17, 1985, abandoned, which is a continuation-in-part of Ser. No. 680,678, Dec. 12, 1984, abandoned, which is a continuation-in-part of Ser. No. 576,233, Feb. 2, 1984, abandoned.

[51] Int. Cl.$^4$ ............... A61K 31/445; C07D 491/147; C07D 495/14
[52] U.S. Cl. ............................ 514/285; 514/212; 514/222; 514/229; 514/231; 514/234; 514/253; 514/291; 540/597; 544/58.4; 544/125; 544/126; 544/357; 544/361; 544/405; 546/62; 546/80; 546/89; 546/92

[58] Field of Search ............ 546/62, 80, 89, 92; 540/597; 544/58.4, 125, 126, 357, 361, 405; 514/212, 222, 229, 231, 234, 253, 291, 285

[56] References Cited

FOREIGN PATENT DOCUMENTS

| 1435573 | 5/1976 | United Kingdom | 546/70 |
| 2083029A | 3/1982 | United Kingdom | 546/95 |
| 2106909 | 4/1983 | United Kingdom | 546/95 |

OTHER PUBLICATIONS

Burger's Medicinal Chemistry, 4th ed. Pt. III, pp. 307–310.
Opalko et al., Chem. Abst. 96:162676j (1982).
Kluze et al., Chem. Abstr. 91:204200d (1979).

Primary Examiner—Richard A. Schwartz
Attorney, Agent, or Firm—William H. Nicholson; Michael C. Sudol

[57] ABSTRACT

Substituted hexahydro arylquinolizines and pharmaceutically acceptable salts thereof are selective $\alpha_6$-adrenergic receptor antagonists and thereby useful as antidepressants, antihypertensives, antidiabetics, antiobesity and platelet aggregation inhibitors.

51 Claims, No Drawings

SUBSTITUTED HEXAHYDRO ARYLQUINOLIZINES AS α₂ BLOCKERS

BACKGROUND OF THE INVENTION

This is a continuation-in-part of copending application, Ser. No. 755,863, filed July 17, 1985, now abandoned, which in turn is a continuation-in-part of application, Ser. No. 680,678, filed Dec. 12, 1984, now abandoned, which in turn is a continuation-in-part of application Ser. No. 576,233 filed Feb. 2, 1984, now abandoned.

This invention is concerned with novel substituted hexahydro arylquinolizines or pharmaceutically acceptable salts thereof which are selective $\alpha_2$-adrenoceptor antagonists and are of value in conditions where selective antagonism of the $\alpha_2$-adrenoceptor is desirable for example as antidepressant, antihypertensive, antidiabetic, antiobesity agents, or platelet aggregation inhibitors. It also relates to processes for preparing the novel compounds, pharmaceutical compositions comprising the novel compounds and to a method of antagonizing $\alpha_2$-adrenoceptors.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

In addition to $\alpha_1$-adrenergic receptors which mediate postsynaptic responses to the neurotransmitter, norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norepinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

Peripheral $\alpha_2$-adrenoceptors are associated with a variety of important physiological effects. Stimulation of vascular $\alpha_2$-adrenoceptors mediates vasoconstriction and results in hypertension. Pancreatic $\alpha_2$-adrenoceptors modulate release of insulin. Activation of platelet $\alpha_2$-adrenoceptors results in platelet aggregation. $\alpha_2$-adrenoceptors also affect gastrointestinal motility and fat cell metabolism.

Molecules which selectively antagonize these peripheral $\alpha_2$-adrenoceptors offer a novel approach to the treatment of pathological conditions such as hypertension, diabetes, obesity, and disorders involving platelet aggregation and gastrointestinal motility. Because concomitant blockade of both peripheral and central $\alpha_2$-adrenoceptors when central $\alpha_2$-blockade is not the objective can give rise to undesired side effects, agents that do not readily cross the blood-brain barrier are particularly valuable for treatment of those conditions associated with peripheral receptors.

Compounds structurally related to the novel compounds of this invention are disclosed in British Patent Nos. 1,435,573, and 2,106,909 and 2,136,804 of John Wyeth and Brother, Ltd.

DETAILED DESCRIPTION OF THE INVENTION

This invention is concerned with a compound of structural formula I:

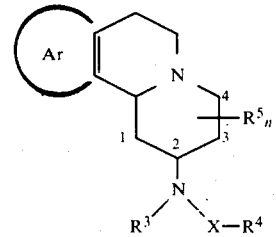

or a pharmaceutical acceptable salt thereof, wherein
Ar represents an aromatic heterocycle such as:

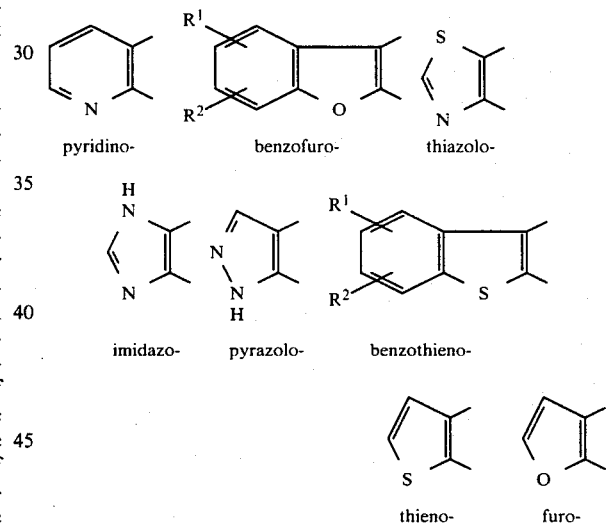

$R^1$ and $R^2$ are independently,
(1) hydrogen,
(2) halo, such as chloro, bromo, or fluoro,
(3) hydroxy,
(4) $C_{1-3}$ alkoxy, or
(5) $C_{1-6}$ alkyl, either straight or branched chain;
$R^3$ is
(1) hydrogen,
(2)

wherein R is hydrogen or $C_{1-3}$ alkyl,
(3) $C_{1-6}$ alkyl, either unsubstituted or substituted with one or more of;
(a) hydroxy,
(b) carboxy, (c) $C_{1-3}$alkoxycarbonyl,
(d) halo such as fluoro, chloro or bromo,
(e) $C_{1-3}$alkoxy,
(f) —$CONR^6R^7$ wherein $R^6$ and $R^7$ are the same or different and are hydrogen or $C_{1-5}$alkyl or joined together either directly to form a 5–7 membered ring such as pyrrolidino, or piperidino, or through a heteroatom selected from N, O, and S, form a 6-membered heterocycle with the nitrogen to which they are attached such as morpholino, piperazino, N-$C_{1-3}$ alkylpiperazino, or
(g) —$NR^6R^7$
(h)

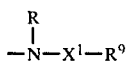

wherein
$X^1$ is

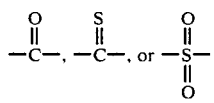

and
$R^9$ is
(i) $C_{1-3}$alkoxy,
(ii) $C_{1-3}$alkyl; or
(iii) —$NR^6R^7$:

X is

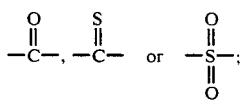

$R^4$ is
(1) —$OR^8$ wherein $R^8$ is hydrogen or $C_{1-6}$ alkyl, either unsubstituted or substituted with one or more of
   (a) —OR, or
   (b) —NRCOR,
(2) —$N(R^8)_2$ wherein the $R^8$ groups are the same or different.
(3) —$CO_2R^8$
(4) —$CONR^6R^7$
(5) $C_{1-6}$alkyl, either unsubstituted or substituted with
   (a) $OR^8$
   (b) halo,
   (c) $CO_2R^8$
   (d) $CONR^6R^7$
(6) $C_{2-5}$alkenyl,
(7) $C_{2-5}$alkynyl,
(8) $C_{3-6}$cycloalkyl,
(9) 5 or 6 membered heterocycle including up to 2 heteroatoms selected from O,N and S, such as imidazo, thiazolo, furanyl, oxazolo, piperidino, piperazino, pyridino, or pyrazino,
(10) carbocyclic aryl, of 6 to 10 carbon atoms such as phenyl or naphthyl, either unsubstituted or substituted with one or more of
   (a) halo,
   (b) OR, or
   (c) $C_{1-3}$alkyl $R^3$ and $R^4$, taken together directly or through a heteroatom selected from O, N and S, form a 5 or 6-membered heterocycle with the nitrogen to which they are attached such as 2-oxazolidinon-1-yl, or succinimidoyl.

$R^5$ is independently
(1) $C_{1-6}$ alkyl, either unsubstituted or substituted with one or more of
   (a) —$OR^8$,
   (b) $NR^8COR^8$, or
   (c) $CO_2R^8$,
(2) —$CO_2R^8$,
(3) —$CONR^6R^7$;
n is 0, 1, 2, or 3; and $R^3$ and $R^5$ or $R^4$ and $R^5$, if $R^5$ is in the 1-or 3-position and both are alkyl, can be joined together to form a 5- or 6-membered ring.

The pharmaceutically acceptable salts coming within the purview of this invention include the pharmaceutically acceptable acid addition salts. Acids useful for preparing these acid addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic, theophylline, 8-chlorotheophylline, p-aminobenzoic, p-acetamidobenzoic, methanesulfonic, or ethanedisulfonic acid.

In a preferred embodiment of this invention, Ar is $R^1,R^2$-benzo[b]furo- or $R^1,R^2$-benzo[b]thieno. It is further preferred that $R^1$ and $R^2$ be hydrogen or halo and $R^3$ be $C_{1-6}$alkyl, especially methyl, and that $R^4$ be $C_{1-6}$alkyl, di($C_{1-3}$ alkyl)amino, halo-$C_{1-6}$ alkyl, hydroxy-$C_{1-6}$ alkyl, $C_{2-5}$ alkenyl, carbocyclic aryl, 5 or 6-membered heterocycle, , —$CO_2R^8$, $C_{1-6}$ alkyl-$CO_2R^8$ or —$C_{1-6}$alkyl-$CONR^6R^7$. It is also preferred that $R^5$ be hydrogen or $C_{1-9}$ alkyl and that X be —$S_2$—.

It is most preferred that $R^1$ and $R^2$ be hydrogen, $R^3$ be methyl, $R^4$ be $C_{1-6}$ alkyl, hydroxypropyl, hydroxyethyl, dimethylamino, $C_{1-3}$ alkoxycarbonylethyl, or dimethylaminocarbonylmethyl, and $R^5$ be hydrogen.

Another embodiment of this invention are those compounds which do not cross the blood-brain barrier easily and are therefore particularly useful for their peripheral activity including the treatment of diabetes, hypertension, and obesity, the inhibition of platelet aggregation and for effect on gastrointestinal motility. The principal non-centrally acting $\alpha_2$-antagonists include those compounds wherein $R^4$ is $C_{1-3}$alkyl, phenyl and 2-furyl, and $R^3$ is $C_{1-3}$ alkyl substituted with

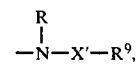

especially wherein X' is —$SO_2$— and $R^9$ is $C_{1-3}$ alkyl.

The novel compounds of this invention are depicted herein as having the configuration in which the hydrogen at C-12b and the nitrogen at C-2 are trans

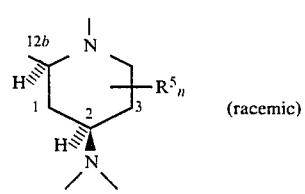

(racemic)

and it is the more preferred isomer for $\alpha_2$-adrenoceptor blockade activity. However, the isomers having the configuration in which the hydrogen at C-12b and the nitrogen at C-2 are cis are also active $\alpha_2$-adrenoceptor blockers and are considered to be within the scope of this invention. Each of the 2RS,12bSR and 2RS,12bRS-configurational isomers are racemates capable of being resolved into dextrorotatory and levorotatory enantiomers. This invention includes these pure enantiomers as well as all mixtures thereof, especially the racemates.

A novel process for preparing novel compounds of this invention comprises acylation (carboxyl or sulfonyl) of the compound of structure IIa:

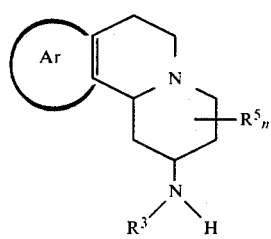

IIa with an acylating reagent such as an acid anhydride, activated ester, mixed acid anhydride or acid halide capable of introducing a substituent of formula $-XR^4$, and preferably wherein the reagent is of structure:

$R^4$-X-halo wherein halo is chloro, bromo or iodo, preferably chloro, and X is

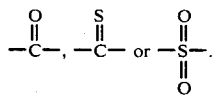

The reaction is conducted in an inert solvent such as a chlorinated hydrocarbon, e.g., methylene chloride, chloroform, 1,2-dichloroethane or the like in the presence of an acid acceptor such as triethylamine, pyridine, an alkali metal carbonate, or basic anion exchange resin. The reaction usually proceeds readily at about room temperature but any temperature from about 0° C. to the boiling point of the reaction mixture is reasonable depending on the reactivity of the particular acyl halide and temperature. Reaction times of about half an hour to about 48 hours are required, and in most cases about one to 18 hours suffices.

In those compounds wherein $-XR^4$ is a carbamoyl or thiocarbamoyl group such as

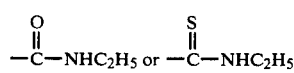

an alternative novel process comprises treatment of compound IIa with the appropriate alkyl isocyanate or isothiocyanate respectively. The synthesis is conducted in an inert organic solvent or lower alkanol such as ethanol, propanol, 1,2-dimethoxyethane or the like at about room temperature (20° C.) to 100° C. for about 5 minutes to about 2 hours.

A further novel process of this invention comprises condensing the intermediate 2-oxo compound with a diaminoalkane followed by reduction and acylation as illustrated by:

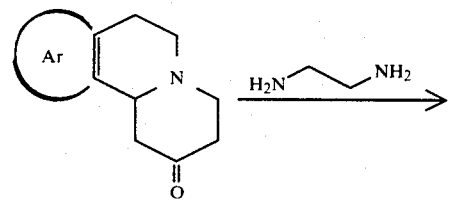

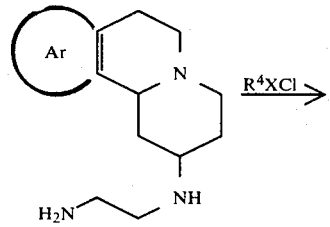

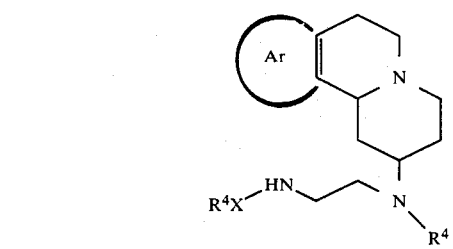

Condensation of the 2-oxo compound as the hydrochloride or similar salt with the diaminoalkane is conducted in a $C_{1-3}$ alkanol in the presence of a mild dehydrating agent or water acceptor such as molecular seives at about 50° C. to the reflux temperature for about 10-24 hours. The alkanolic solution of the Schiff base is then treated with a complex metal anhydride such as $NaBH_4$ at about $-5°$ to $+5°$ C. followed by a bout 0.5 to 2 hours at about 35° to 60° C.

The acylation with R4 X Cl is conducted as previously described

The novel process for the preparation of the compound wherein $R^3$ and $XR^4$ are joined together to form the sultam or lactam substructure:

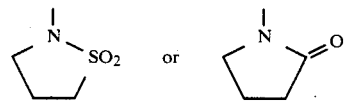

comprises treating the compound with substructure

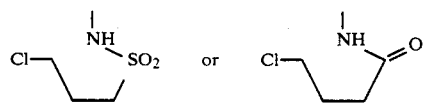

with a strong base such as potassium t-butoxide, n-butyl lithium, sodium hydride or the like in an ethereal solvent such as 1,2-dimethoxyethane, diglyme, THF or the like at about 20° C. to 60° C. for about one to 5 hours.

The novel process for preparing compounds with a imide substructure in the 2-position such as

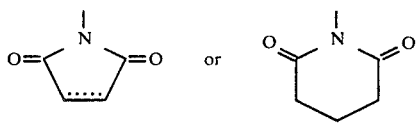

comprises heating compound IIa wherein $R^3$ is hydrogen with the corresponding cyclic dicarboxylic anhydride of structure:

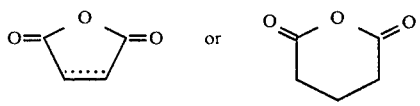

respectively in an inert solvent such as toluene or with no solvent at about 100° to 150° C. for about 2 to 5 hours.

The novel compounds with a cyclic carbamate, cyclic urea or cyclic sulfamide in the 2-position of structures:

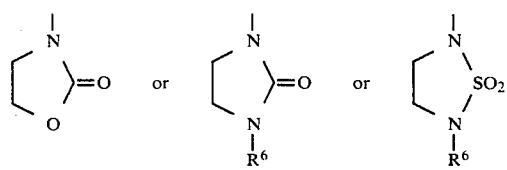

are prepared by treating the compound with substructure:

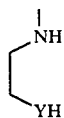

IIb wherein Y is —O— or $NR^6$ with carbonyl diimidazole or sulfuryl chloride in an inert solvent such as dimethoxyethane, methylene chloride or the like at about 20° to 60° C. in the presence of an acid acceptor such as triethylamine, di(isopropyl)ethylamine or the like for about 5 to 18 hours.

In the novel method of selectively antagonizing $\alpha_2$-adrenergic receptors in a patient, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

The novel compounds of this invention can be administered as the sole active ingredient or in combination with other antidepressants such as amitriptyline, imipramine or other norepinephrine or serotonin reuptake inhibitor or a monoamine oxidase inhibitor.

These doses are useful for treating depression, diabetes, hypertension, obesity and abnormal platelet aggregation.

The compounds, or pharmaceutically acceptable salts thereof, of the present invention, in the described dosages, are administered orally, intraperitoneally, subcutaneously, intramuscularly, transdermally or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

(2SR,12bRS)-N-(1,3,4,6,7,12b-Hexahydro-2H-benzo[b]furo[2,3-a]quinolizin-2-yl)-N,N',N'-trimethylsulfamide Step A: Preparation of 3-Cyanomethylbenzo[b]furan To a suspension of 2.64 gms (0.11 mole) of oil free sodium hydride in 200 ml of tetrahydrofuran (THF) was added dropwise a solution of 19.47 gms (0.11 mole) of diethylcyanomethylphosphonate in 75 mL of THF. After the $H_2$ evolution had ceased, a solution of 13.4 g (0.1 mole) of 3-(2H)-benzo[b]furanone in 100 mL of THF was added. The solution was heated at 70° C. for 1.5 hours, cooled, and poured into 500 mL of 5% HCl, and washed with ether. The ether phase was washed with brine, dried ($MgSO_4$), filtered and concentrated to give 15.4 g of a dark oil. The product was distilled at 96°-100° C./0.075 mm Hg to give 10.85 g of a yellow oil which crystallized upon standing.

Step B: Preparation of 2-(3-benzo[b]furanyl)ethylamine

A solution of 3.97 g (0.025 mole) of 3-cyanomethylbenzo[b]furan in 200 mL of diethyl ether was slowly added to a refluxing suspension of 3.84 g (0.1 mole) of lithium aluminum hydride in 400 mL of ether. The reaction was heated 3 hours., cooled and water was slowly added. The suspension was filtered through a pad of filter aid and the filtrate was evaporated to give 3.2 g of oily product. The hydrochloride salt has m.p. 183°-185° C.

Step C: Preparation of 3-(2-Formamidoethyl)benzo[b]furan

A solution of 2.35 g (0.015 mole) of 2-(3benzo[b]furanyl)ethylamine and 5 mL of ethyl formate was heated at 60° C. for 3 hours, poured into 2N HCl and washed with methylene chloride which in turn was washed with 5% sodium hydroxide (w/v), dried ($MgSO_4$), filtered and concentrated to give 2.70 g of product.

Step D: Preparation of 3,4-dihydrobenzo[b]furo[2,3-c]pyridine 2.28 Grams (0.012 mole) of 3-(2-formamidoethyl)benzo[b]furan was added to 28 g of polyphosphoric acid which was preheated to 100° C. After 1-1.5 hours, the reaction mixture was poured onto ice and the residues were washed with water. The polyphosphoric acid was dissolved in water, filtered through a pad of celite and made basic with concentrated ammonia. A precipitate was collected and dried to give 1.45 g of product, m.p. 170°-171° C.

Step E: Preparation of (12bRS)-1,3,4,6,7,12b-Hexahydrobenzo[b]furo[2,3-a]quinolizin-2-one To a solution of 12 g (0.070 mol) of 3,4-dihydrobenzo[b]furo[2,3-c]pyridine dissolved in 500 mL of acetonitrile at 60° C. was added 20 g (0.140 mol) of 2-trimethylsiloxy-1,3-butadiene followed by 13.6 g (0.10 mol) of anhydrous zinc chloride. The mixture was heated at 60° C. for 1.5 hour, cooled to 25° C., and 30 mL of 5% HCl was added and stirred 10 minutes. 40% Sodium hydroxide was added until the reaction was basic; 200 mL of water was added; and the acetonitrile layer was separated. The aqueous layer was filtered through celite and washed with ether. The combined organic layers were dried (Na₂SO₄), filtered, and concentrated to a brown residue which was chromatographed (silica, ethyl acetate/hexane (1:1)) to give 8.2 g of product, m.p. 108°–9° C.

Resolution of (12bSR)-1,3,4,6,7,12b-hexahydrobenzo[b]furo2,3-a]quinolizin-2-one

A solution of (−)-di-p-toluoyl-L-tartaric acid monohydrate (25.9 g) in 100 ml of ethyl acetate was mixed with a solution of (12bSR)-1,3,4,6,7,12b-hexahydrobenzo[b]furo[2,3-a]quinolizin-2-one (15.5 g) in 700 ml of ethyl acetate and allowed to stand 12–78 hours. The mixture was filtered to yield 21 g of the di-p-toluoyl-L-tartrate salt of the amine. The free base was liberated by partitioning between aqueous Na₂CO₃ and ethyl acetate ([α]$_D$=ca. −79°; C=0.001, CHCl₃). The diasteriomeric salt of this material was again prepared following the above procedure. The collected di-p-toluoyl-L-tartrate salt was partitioned between ethyl acetate and aqueous Na₂CO₃, dried (Na₂SO₄), filtered, treated with charcoal, filtered and evaporated to yield 5.4 g (35%) of (12bS)-1,3,4,6,7,12b-hexahydrobenzo[b]furo[2,3-a]quinolizin-2-one; [α]$_D$ = −84°; (C=0.001, CHCl₃).

The (12bR)-1,3,4,6,7,12b-hexahydrobenzo[b]furo[2,3-a]quinolizin-2-one was obtained by substituting (+)-di-p-toluoyl-D-tartaric acid monohydrate for (−)-di-p-toluoyl-L-tartaric acid in the above procedure to provide product with [α]$_D$ = +84° (C=0.001, CHCl₃).

Employing the procedures substantially as described in Example 1, Steps A through E, or in some cases, Steps C through E but substituting for the 3-benzofuranone used in Step A thereof the ketones described in Table I, or for the ethylamines used in Step C thereof, the corresponding ethylamines described in Table I, or for the butadienes used in Step E thereof, the corresponding substituted butadienes described in Table I, there are prepared the Ar[2,3-a]quinolizin-2-ones, also described in Table I by the following reactions:

TABLE I

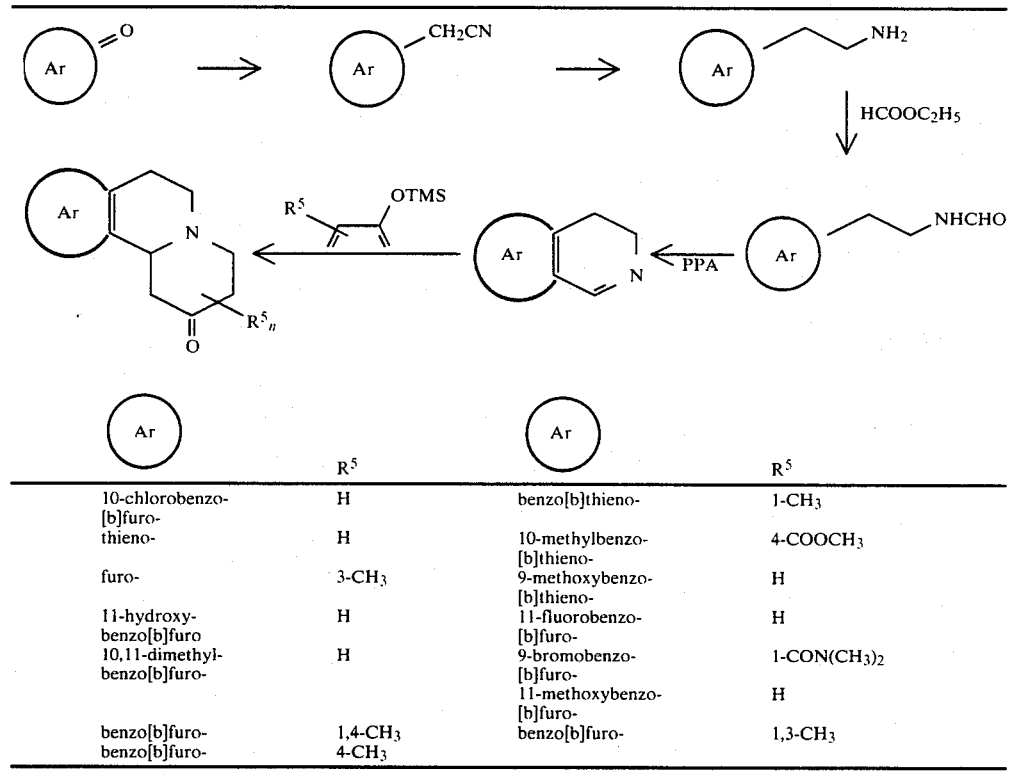

| Ar | R⁵ | Ar | R⁵ |
|---|---|---|---|
| 10-chlorobenzo[b]furo- | H | benzo[b]thieno- | 1-CH₃ |
| thieno- | H | 10-methylbenzo[b]thieno- | 4-COOCH₃ |
| furo- | 3-CH₃ | 9-methoxybenzo[b]thieno- | H |
| 11-hydroxybenzo[b]furo | H | 11-fluorobenzo[b]furo- | H |
| 10,11-dimethylbenzo[b]furo- | H | 9-bromobenzo[b]furo- | 1-CON(CH₃)₂ |
|  |  | 11-methoxybenzo[b]furo- | H |
| benzo[b]furo- | 1,4-CH₃ | benzo[b]furo- | 1,3-CH₃ |
| benzo[b]furo- | 4-CH₃ |  |  |

Step F: Preparation of (2SR,12bRS)-N-(1,3,4,6,7,12b-hexahydro-2H-benzo[b]furo[2,3-a]quinolizin-2-yl)-N-methylamine To a solution of 2.41 g (0.010 mol) of (12bRS)-1,3,4,6,7,12b-hexahydrobenzo[b]furo[2,3-a]-quinolizin-2-one dissolved in 60 mL of ether and 40 mL of benzene cooled to 0° C. was added 5 mL of methylamine followed by a solution of 0.56 mL (0.052 mol) of titanium tetrachloride in 3 mL of benzene. The reaction was stirred at 0° C. for 30 minutes, warmed to 25° C. and stirred 2 hours. The mixture was filtered through a pad of celite, and the salts were washed with benzene/ether (2:1). The filtrate was evaporated, giving 2.55 g of an oil. The oil was dissolved in 80 mL of ethanol and 0.38 g (0.010 mol) of sodium borohydride was added. The solution was stirred 18 hours, and 100 mL of water was added. Stirring was continued for 30 minutes; the ethanol was evaporated in vacuo and the aqueous phase was extracted with methylene chloride which was dried (Na₂SO₄), filtered, and concentrated, giving 2.56 g of product. The product was purified by chromatography (silica gel, chloroform saturated with NH₃) to yield 1.77 g of product. The dihydrochloride salt obtained from ethanolic HCl has m.p. 300° C.

Employing the procedures described in Step F hereof but starting with the substantially enantiomerically pure quinolizin-2-ones from Step E there were produced:

(2R,12bS)-N-(1,3,4,6,7,12b-hexahydro-2H-benzo[b]furo[2,3-a]quinolizin-2-yl)-N-methylamine, m p. 77–79 C., [α]$_{589}$ −66° (CHCl₃); and (2S,12bR)-N-(1,3,4,6,7,12b-hexahydro-2H-benzo[b]furo[2,3-a]quinolizin-2-yl)-N-methylamine, m.p. 77-79 C., $[\alpha]_{589}$ +66° (CHCl$_3$).

Employing the procedure substantially as described in Example 1, Step F but substituting for the intermediates and reagents used therein, the Ar[2,3-a]quinolizin-2-ones and the amines of structure R$^3$NH$_2$, described in Table II, there are prepared the N-(Ar[2,3-a]quinolizin-2β-yl)-N-R$^3$-amines, also described in Table II by the following reaction.

Step G: Prepartion of (2SR,12bRS)-N-(1,3,4,6,7,12b-hexahydro-2H-benzo[b]furo[2,3-a]quinolizin-2-yl)-N,N',N'-trimethylsulfamide HCl To a solution of 2.54 g (0.01 mol) of amine from Step F in 50 mL of methylene chloride was added 2.00 g (0.020 mol) of triethylamine followed by 2.80 g (0.02 mol) of dimethylsulfamoyl chloride. The mixture was stirred for 36–48 hours and then poured into 100 mL of 5% (w/v) NaOH which was then extracted with methylene chloride. The organic layer was dried (Na$_2$SO$_4$), filtered and concentrated to give 3.75 g of an oil which was chromatographed (silica/2% CH$_3$OH/CHCl$_3$) to give 2.92 g of product. The free base was acidified with ethanolic HCl. Addition of ether afforded the hydrochloride, m.p. 256°-257° C.

Employing the procedure substantially as described in Example 1, Step G but substituting for the racemic amine from Step F equal amounts of the substantially enantiomerically pure amines there were produced the (2R,12bS)-trimethylsulfamide;

$[\alpha]_{589}$ $^{20}$ (free base) +17° (C=0.001, pyridine); m.p. (HCl salt) 263°-264° C.; and (2S,12bR)-N-1,3,4,6,7,12b-hexahydro-2H-benzo[b]furo[2,3-a]quinolizin-2-yl)-N,N',N'-trimethylsulfamide;
$[\alpha]_{589}$ $^{20}$ (free base) −17° (C=0.001, pyridine); m.p. (HCl salt) 263°-264° C.

Employing the procedure substantially as described in Example 1, Step G, but substituting for the dimethylsulfamoyl chloride and the amine used therein comparable amounts of the compounds R$^4$-X-Cl and the amines described in Table III there are produced the (R$^3$)(R$^4$X) amines, also described in Table III, in accordance with the following reaction:

TABLE II

| Ar | R$^3$ | R$^5$ |
|---|---|---|
| 11-fluorobenzo[b]furo- | CH$_3$— | H |
| thieno- | n-C$_3$H$_7$— | H |
| furo- | (CH$_3$)$_2$NCOCH$_2$— | 1-CH$_3$ |
| 11-hydroxybenzo[b]furo- | CH$_3$— | H |
| 10,11-dimethylbenzo[b]furo- | CH$_3$NHC$_2$H$_4$— | 3-COOCH$_3$ |
| benzo[b]thieno- | CH$_3$OCH$_2$CH$_2$— | H |
| 10-methylbenzo[b]thieno- | CH$_3$— | H |
| 9-methoxybenzo[b]thieno- | C$_2$H$_5$— | 4-CON(Me)$_2$ |
| 10-chlorobenzo[b]thieno- | C$_2$H$_5$O$_2$CCH$_2$— | H |
| 9-bromobenzo[b]furo- | H— | 4-CH$_3$ |
| 11-methoxybenzo[b]furo- | C$_2$H$_5$— | H |
| benzo[b]furo- | HOC$_2$H$_4$— | 3-CH$_3$ |
| benzo[b]furo- | n-C$_3$H$_7$— | H |
| benzo[b]furo- | H$_2$NOCH$_2$C— | H |
| benzo[b]furo- | CH$_3$CO— | 1-COOCH$_3$ |
| benzo[b]furo- | ClCH$_2$CH$_2$CH$_2$— | H |
| benzo[b]furo- | CH$_3$ | 1,4-CH$_3$ |
| benzo[b]furo- | CH$_3$ | 1,3-CH$_3$ |

TABLE III

| Ar | R$^3$ | X | R$^4$ | R$^5$ | Reaction time (Hours) | Salt mp (°C.) |
|---|---|---|---|---|---|---|
| benzo[b]furo | —CH$_3$ | —SO$_2$— | —CH$_2$CH(CH$_3$)$_2$ | H | 3 | HCl, 237-239 |
| benzo[b]furo | —CH$_3$ | —CO— | —CH$_2$CH$_3$ | H | 1 | HCl, 1.5H$_2$O 165-170 |

TABLE III-continued

| Ar | R³ | X | R⁴ | R⁵ | Reaction time (Hours) | Salt mp (°C.) |
|---|---|---|---|---|---|---|
| benzo[b]furo | —CH₃ | —CO— | —CH₂CH(CH₃)₂ | H | 1 | HCl, 0.5₂O 223–226 |
| benzo[b]furo | —CH₃ | —CO— | —C(=O)—OCH₃ | H | 1 | HCl, 0.25H₂O 204–206 |
| benzo[b]furo | —CH₃ | —CO— | —N(CH₃)₂ | H | 48 | HCl, 0.75H₂O 174–177 |
| benzo[b]furo | —CH₃ | —CO— | —OC₂H₅ | H | 0.5 | HCl, 0.75H₂O 240–243 |
| benzo[b]furo | —CH₃ | —CO— | —C(=O)—OC₂H₅ | H | 18 | HCl, 225 |
| (2R,12bS)benzo[b]furo | —CH₃ | —SO₂ | —CH₂Cl | H | 18 | HCl, 168–170 |
| benzo[b]furo | —CH₃ | —CO— | furyl | H | 1.5 | HCl, 0.5H₂O 275–280 |
| benzo[b]furo | —CH₃ | —SO₂— | 2-pyridyl | H | 18 | HCl, 250 |
| benzo[b]furo | —CH₃ | —CO— | phenyl | H | 18 | HCl, 0.5H₂O 250 |
| benzo[b]furo | —CH₃ | —CO— | (2,2-dimethyl-1,3-dioxolan-4-yl)methoxymethyl | H | | |
| benzo[b]furo | —CH₃ | —SO₂— | CH₂CH₂OH | H | | HCl, 250 |
| benzo[b]furo | —CH₃ | —CO— | —CO—N(CH₃)₂ | H | | HCl, 325 |
| benzo[b]furo | HOCH₂CH₂— | —SO₂ | —N(CH₃)₂ | H | | HCl, 0.5H₂O |
| benzo[b]furo | —CH₃ | —SO₂ | —CH=CH₂ (vinyl) | H | | HCl, 0.5H₂O 248 |
| benzo[b]furo | —CH₃ | —SO₂— | C₂H₅— | H | | HCl, 257–260 |
| benzo[b]furo | n-C₃H₇ | —SO₂ | —N(CH₃)₂ | H | | HCl, 160 |
| benzo[b]furo | —CH₃ | —SO₂ | CH₂CH₂COOCH₃ | H | | HCl, 227–28 |
| benzo[b]furo | —CH₃ | —CO— | CH₂COOC₂H₅ | H | | HCl, 202–04 |
| benzo[b]furo | —CH₃ | —CO— | CH₂OCH₃ | H | | HCl, 227–28 |
| benzo[b]furo | —CH₂CONH₂ | —SO₂— | —N(CH₃)₂ | H | | HCl, 1.5H₂O 225–227 |
| benzo[b]furo | —CH₃ | —SO₂— | CH₂CH₂CH₂Cl | H | | HCl, 234–236 |

TABLE III-continued

| Ar | R³ | X | R⁴ | R⁵ | Reaction time (Hours) | Salt mp (°C.) |
|---|---|---|---|---|---|---|
| benzo[b]furo | CH₃— | —CO— | ![pyrrolidine-CO-N] CO—N⟨⟩ | H | | HCl, 240–243 |
| benzo[b]furo | CH₃— | —SO₂— | 2-furyl | H | | HCl, 270–275 |
| benzo[b]thieno | CH₃— | —SO₂— | C₂H₅ | H | | HCl, 240 |
| benzo[b]furo | CH₃— | —SO₂— | 2-thienyl | H | | HCl, 270 |
| benzo[b]furo | CH₃— | —SO₂— | CH₂COOC₂H₅ | H | | HCl, 0.5H₂O 147–150 |
| benzo[b]furo | CH₃— | —SO₂— | 2-thiazolyl | H | | HCl, 260 |
| 11-fluorobenzo[b]furo | CH₃— | —SO₂ | cyclopentyl | 3-CH₃ | | |
| 11-methoxybenzo[b]furo | C₂H₅— | —SO₂— | —N⟨⟩S→O (thiomorpholine S-oxide) | 4-CH₃ | | |
| benzo[b]thieno | CH₃— | —CO— | 2-pyrazinyl | H | | |
| benzo[b]furo- | CH₃— | —SO₂— | CH₃ | 1,4-CH₃ | | |
| benzo[b]furo- | CH₃— | —SO₂— | CH₃ | 1,3-CH₃ | | |
| benzo[b]furo | CH₃— | —SO₂— | —CH₂CON(CH₃)₂ | H | | HCl, 0.5H₂O 151–153 |
| benzo[b]furo | —CH₃ | —CO— | 1-methyl-2-pyrrolyl | H | 12 | 2HCl, 280–284 |
| benzo[b]furo | —CH₃ | —SO₂— | o-tolyl | H | 16 | HCl, 290–294 |
| 10-chlorobenzo[b]furo | —CH₃ | —SO₂— | —C₂H₅— | H | 14 | HCl, 262–264 |
| benzo[b]furo | —CH₃ | —CO— | 2-furyl | H | 3 | HCl, 305–310 |
| benzo[b]furo | —CH₃ | —SO₂— | —CH₃ | H | 4 | HCl, 255(dec) |

TABLE III-continued

| Ar | R³ | X | R⁴ | R⁵ | Reaction time (Hours) | Salt mp (°C.) |
|---|---|---|---|---|---|---|
| (2R,12bS)benzo[b]furo | —CH₃ | —SO₂— | —N(CH₃)₂ | H | 18 | HCl, 263–264 |
| benzo[b]furo | —CH₃ | —SO₂— | —CH₂Ph | H | 8 | HCl, 255–265 |
| 11-methoxybenzo[b]furo | —CH₃ | —SO₂— | —Et | H | 10 | HCl, 244–247 |
| (2S,12bR)benzo[b]furo | —CH₃ | —SO₂— | —N(CH₃)₂ | H | 18 | HCl, 263–264 |
| benzo[b]thieno | —CH₃ | —SO₂— | —CH₂CH₂OH | H | 2 | HCl, 0.5H₂O 164–167 |
| benzo[b]thieno | —CH₃ | —SO₂— | —CH₃ | H | 4 | HCl, 250 |
| 11-chlorobenzo[b]furo | —CH₃ | —SO₂— | —C₂H₅— | H | 3 | HCl, 0.5H₂O, 256–259 |
| benzo[b]thieno | —CH₃ | —SO₂— | —N(CH₃)₂ | H | 18 | HCl, 265–268 |
| 9-chlorobenzo[b]furo | —CH₃ | —SO₂— | —C₂H₅— | H | 4 | HCl, 280 |
| (2S,12bR)benzo[b]furo | —CH₃ | —SO₂— | —CH₂CH₂OH | H | 1 | HCl, 265(dec) |
| (2R,12bS)benzo[b]furo | —CH₃ | —SO₂— | —CH₂Ch₂OH | H | 1 | HCl, 265(dec) |
| (2R,12bS)benzo[b]furo | —CH₃ | —SO₂— | —CH₃ | H | 1 | HCl, 280–284 |
| benzo[b]furo | —CH₃ | —SO₂— | —NH—CH(CH₃)₂ | H | 18 | HCl, 225–227 |
| benzo[b]furo | —CH₃ | —SO₂— | —N(CH₃)CH₂CH₂OH | H | 24 | HCl, 0.5H₂O 214–216 |
| 9-methoxybenzo[b]furo | —CH₃ | —SO₂— | —C₂H₅— | H | 5 | HCl, 231–234 |
| 10-methoxybenzo[b]furo | —CH₃ | —SO₂— | —C₂H₅ | H | 4 | HCl, H₂O, 240–242 |
| 9-methoxybenzo[b]furo | —CH₃ | —SO₂— | —N(CH₃)₂ | H | 18 | HCl, .75H₂O, 234–236 |
| 10-methoxybenzo[b]furo | —CH₃ | —SO₂— | —N(CH₃)₂ | H | 18 | HCl, 247–248 |
| thieno | —CH₃ | —SO₂— | —N(CH₃)₂ | H | 18 | HCl, 0.25H₂O, 243–245(dec) |
| benzo[b]furo | —CH₃ | —SO₂— | —N(CH₃CH₂OH)₂ | H | 24 | 0.5H₂O, 140–142 |
| thieno | —CH₃ | —SO₂— | —C₂H₅ | H | 8 | HCl, H₂O, 247–250 |
| 10-chlorobenzo[b]furo | —CH₃ | —SO₂— | —N(CH₃)₂ | H | 16 | HCl, 0.25H₂O |
| 10-methylbenzo[b]thieno | —CH₃ | —SO₂— | —C₂H₅ | H | 6 | HCl, 280 |
| 11-chlorobenzo[b]thieno | —CH₃ | —SO₂— | —C₂H₅ | H | 4 | HCl, 278–281 |
| 11-chlorobenzo[b]thieno | —CH₃ | —SO₂— | —N(CH₃)₂ | H | 18 | HCl, 246–248 |
| 9-hydroxybenzo[b]furo | —CH₃ | —SO₂— | —C₂H₅ | H | 3 | HCl, 301–304 |
| 11-isopropyl-benzo[b]thieno | —CH₃ | —SO₂— | —C₂H₅ | H | 6 | HCl, 228–230 |
| benzo[b]furo | —CH₃ | —SO₂— | —CH₃ | 1α-CH₃ | 2 | HCl, 0.25H₂O; 270–273 |
| benzo[b]furo | —CH₃ | —SO₂— | —CH₃ | 3α-CH₃ | 2 | HCl, 0.25H₂O; 262–264 |
| benzo[b]furo | —CH₃ | —SO₂— | —CH₃ | 1β-CH₃ | 2 | HCl, 0.5H₂O; 250–252 |
| benzo[b]furo | CH₃— | —SO₂ | —N(CH₂CH₂)₂N—CH₃ | 1-CH₃ | | |
| 9-methoxybenzo[b]thieno | C₂H₅ | —CO— | —CH₂CH₂CH₂—NH₂ | 3-C₂H₅ | | |

TABLE III-continued

| Ar | R³ | X | R⁴ | R⁵ | Reaction time (Hours) | Salt mp (°C.) |
|---|---|---|---|---|---|---|
| thieno— | n-C₃H₇ | —SO₂— | 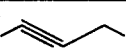 | 1-C₃H₇ | | |
| furo- | (CH₃)₂NCOCH₂— | —SO₂— | 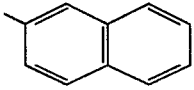 | H | | |
| 11-hydroxybenzo[b]furo | CH₃— | —SO₂— | 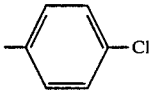 | 4-COOCH₃ | | |
| 10,11-dimethyl-benzo[b]furo- | CH₃NHC₂H₄ | —SO₂— | 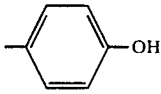 | H | | |
| 10-methylbenzo-[b]thieno- | CH₃— | —SO₂— | 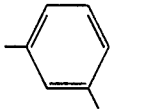 | 1-COOCH₃ | | |
| 10-chlorobenzo-[b]thieno- | —C₂H₅CO₂CH₃ | —SO₂— | —CH₃ | H | | |
| 9-bromobenzo-[b]furo | H— | —SO₂— | —C₂H₅ | H | | |
| benzo[b]furo | CH₃CO— | —SO₂— | $-CH_2\overset{O}{\overset{\|}{C}}N(CH_3)_2$ | 3-CH₂Ph | | |
| benzo[b]furo | Cl(CH₂)₃— | —SO₂— | n-C₃H₇ | H | | |

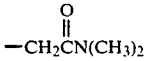

| benzo[b]furo | —CH₃ | —CO— | —CH₂—CH₂— |
| benzo[b]furo | —CH₃ | —SO₂— | —CH₂ |

EXAMPLE 2

(2SR, 12bRS)-N-(1,3,4,6,7,12b-hexahydro-2H-benzo[b]furo[2,3-a]quinolizin-2-yl)-N-methyl-2-hydroxyethanesulfonamide Solutions of 2-hydroxyethanesulfonyl chloride (20.2 g; 0.14 mol) in 100 ml of acetonitrile and triethylamine (14.3 g; 19.7 ml; 0.14 mol) in 100 ml of methylene chloride were added simultaneously by means of a dual syringe drive to a solution of amine from Step F of Example 1 (17.9 g; 0.07 mol) in 1600 ml of a 1:1 mixture of acetonitrile and methylene chloride. After 15 minutes, the solvent was evaporated and the residue was partitioned between methylene chloride and water. The organic phase was separated and washed with water, brine and dried (Na₂SO₄). The solvent was evaporated and the residue was chromatographed over silica gel (CHCl₃ saturated with NH₃). The product obtained (14 g; 55%) was converted to give the product as the hydrochloride salt; m.p. 250° C. (dec).

By employing the procedure substantially as described above but substituting for racemic amine from Step F equal amounts of the enantiomerically pure amines there were produced the hydrochloride salts of the (2R,12bS)-sulfonamide, m.p. 265° C., [α]₅₈₉+13° (C=0.001; CH₃OH); and the (2S,12bR)sulfonamide, m.p. 265° C. [α]₅₈₉—13° (C=0.001;CH₃OH) sulfonamide.

EXAMPLE 3

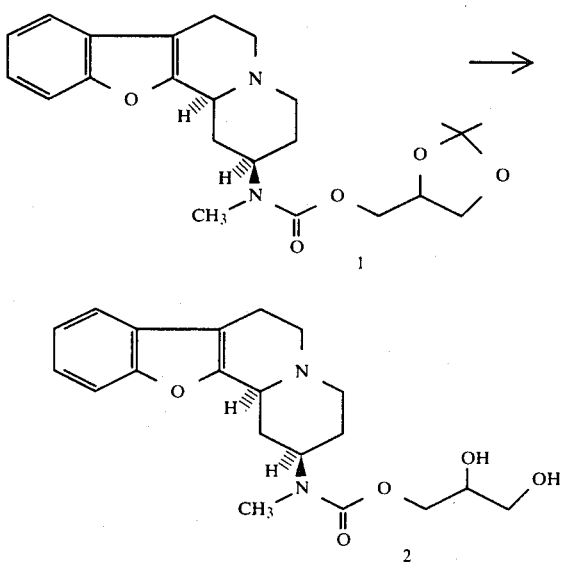

(2SR,12bRS)-1-(2,3-DihydroxyPropyl)-N-(1,3,4,6,7,12b-hexahydro 2H-benzo[b]furo[2,3-a]quinolizin-2-yl)-N-methyl-carbamate oxalate The carbamate, n (0.324 g, 0.723 mmole) was dissolved in 5 mL of acetone and 5 mL of 3N HCl and was stirred at room temperature for 30 minutes; made basic with 40% NaOH; and was extracted with methylene chloride. The extract was dried, filtered and concentrated. The crude oil obtained was purified by spinning plate chromatography (NH$_3$ sat'd CHCl$_3$) to give 0.185 g of product (63%). The monoxalate salt has m.p. 83°–86° C.

EXAMPLE 4

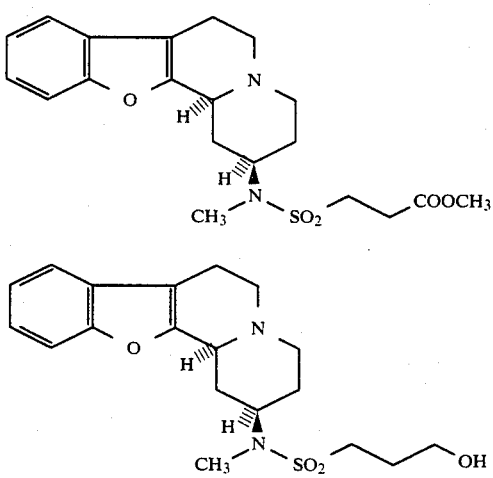

(2SR,12bRS)-N-(1,3,4,6,7,12b-Hexahydro-2H-benzo[b]furo[2,3-a]quinolizin-2-yl)-N-methyl-3hydroxypropane-sulfonamide To the ester, 3, (0.130 g, 0.32 mmole) dissolved in 10 mL of ether at 0° C. was added 0.016 g (0.42 mmole) of lithium aluminum hydride. After 30 minutes, the reaction was poured into dilute HCl and made basic with 40% NaOH. The aqueous solution was extracted with methylene chloride and the extract was dried, filtered and concentrated to an oil. The oil was chromatographed on a spinning plate (2% acetone/ethyl acetate) to give 0.100 g of product (82%). The HCl salt has m.p. 239°–241° C.

EXAMPLE 5

Preparation of (2SR,12bRS)-2-[N'-(1,3,4,6,7,12b-Hexahydro-2H-benzo[b]furo[2,3-a]quinolizin-2-yl)-N'-methylaminosulfonyl]N,N-dimethyl acetamide hydrochloride hemihydrate.

Dimethylamine hydrochloride (0.222 g, 2.72 mmole) was slurried in 20 mL of dry benzene and cooled to 0° C. To this was added 1.36 mL (2.72 mmol) of 2N trimethyl aluminum in toluene. After stirring at room temperature for 1.5 hours, 0.275 g (0.68 mmol) of (2RS,12bSR)-ethyl 2-([N-(1,3,4,6,7,12b-hexahydro-2H-benzo[b]furo[2,3-a]quinolizin-2-yl)-N-methylaminosulfonyl]acetate was added dropwise in 2 mL of benzene. After refluxing 18 hour, the reaction was cooled and 1% HCl was added until gas evolution ceased. The mixture was made alkaline with solid Na$_2$CO$_3$, filtered through a filter pad, and washed with 25 ml of ethyl acetate. The layers were separated and the aqueous layer was extracted with 3×10 mL of ethyl acetate. The organic fractions were combined, washed with water and saturated sodium chloride, dried (Na$_2$SO$_4$) and evaporated to dryness. Medium pressure column chromatography over silica gel, eluting with ethyl acetate gave 0.06 g (0.15 mmol) of starting ester. Continued elution with 5% (v/v) CH$_3$OH/CHCl$_3$ afforded 0.136 g (0.33 mmol) of the dimethyl acetamide in 62.2% yield based on ester consumed. This was dissolved in ether and ethanolic HCl was added dropwise to give a white solid, m.p , 151°–153° C. (acetone/hexane).

EXAMPLE 6

(2SR,12bRS)-N-(1,3,4,6,7,12b-Hexahydro-2H-benzo[b]furo[2,3-a]quinolizin-2-yl)-N-methyl-N'-ethyl urea.HCl.H$_2$O 0.100 Grams (0.39 mmol) of (2SR,12bRS)-N-(1,3,4,6,7,12b-hexahydro-2H-benzo[b]furo-[2,3-a]-quinolizin-2-yl)-N-methylamine was dissolved in 3 mL of ethanol and 0.5 mL of ethyl isocyanoate. The reactants were heated to 60° C. for 10 minutes and then evaporated to dryness to give 0.110 g of product. The hydrochloride salt monohydrate melts at m.p. 199°–202° C.

Employing the procedure substantially as described in Example 6 but substituting for the amine and the ethyl isocyanate used therein, the amines and isocyanates described in Table IV there are produced the ureas, also described in Table IV, by the following reaction:

TABLE IV

[Reaction scheme: Ar-substituted hexahydroquinolizine with NHR³H group + R⁶NCO → urea product with R³N-C(O)-NH-R⁶]

| Ar | R³ | R⁶ |
|---|---|---|
| benzo[b]furo- | —CH₃ | t-C₄H₉— |
| 11-methoxybenzo[b]furo- | —C₂H₅ | CH₃— |
| benzo[b]thieno- | —CH₃ | iso-C₂H₇— |
| 11-chlorobenzo[b]furo- | —CH₃ | C₂H₅— |

EXAMPLE 7

(2SR,12bRS)-N-(1,3,4,6,7,12b-Hexahydro-2H-benzo[b]-furo[2,3-a]quinolizin-2-yl)-N-methyl-N'-ethylthiourea.HCl.0.5H₂O 0.100 Grams (0.39 mmol) of amine from Example 1, Step F is dissolved in 3 mL of dimethoxyethane and 0.5 mL of ethyl isothiocyanate. After 20 minutes, the reaction is evaporated to give the product (0.110 g). The hydrochloride salt hemihydrate melts at 199°–201° C.

Employing the procedure substantially as described in Example 7 but substituting for the amine and the ethylisothiocyanate used therein, the amines and isocyanates described in Table V there are produced the thioureas, also described in Table V, by the following reaction:

TABLE V

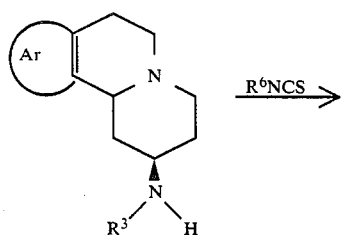

TABLE V-continued

[Reaction product: Ar-substituted hexahydroquinolizine with R³N-C(S)-NHR⁶ group]

| Ar | R³ | R⁶ |
|---|---|---|
| benzo[b]furo- | CH₃— | t-C₄H₉— |
| benzo[b]furo- | n-C₃H₇— | C₂H₅— |
| benzo[b]thieno- | CH₃— | CH₃— |
| 10-chlorobenzo[b]thieno- | C₂H₅O₂CCH₂— | iso-C₃H₇— |
| furo- | (CH₃)₂NCOCH₂— | CH₃— |

EXAMPLE 8

(2SR,12bRS)-N-(1,3,4,6,7,12b-Hexahydro-2H-benzo[b]furo[2,3-a]quinolizin-2-yl)-2-methylpropane sulfonamide.HCl Step A: Preparation of (2SR,12bRS)-N-(1,3,4,6,7,12b-hexahydro-2H-benzo[b]furo[2,3-a]quinolizin-2-yl)-amine To a solution of (2SR)-1,3,4,6,7,12b-hexahydrobenzo[b]furo[2,3-a]quinolizin-2-one (0.10 g, 0.41 mmol) in 5 mL of methanol was added 0.224 g (2.9 mmol) of ammonium acetate and 0.027 g (0.41 mmol) of sodium cyanoborohydride. The reaction was stirred at 25° C. for 24 hours; the methanol was evaporated; the residue was stirred in 6N HCl for 30 minutes, diluted with 30 mL of water and extracted with methylene chloride. The aqueous layer was made basic and extracted with methylene chloride and the extract was dried (Na₂SO₄), filtered and concentrated to 0.065 g of product as a 68/28 ratio of β/α amines.

Step B: Preparation of (2SR,12bRS)-N-(1,3,4,6,7,12b-hexahydro-2H-benzo[b]furo[2,3-a]quinolizin-2yl)-2-methylpropane sulfonamide To 0.080 g (0.33 mmol) of the above amine mixture in 3 mL of methylene chloride was added 0.050 g (0.50 mmol) of triethylamine and 0.078 g (0.50 mmol) of isobutylsulfonylchloride. The mixture was stirred 2 hours, poured into 5% NaOH and washed with methylene chloride which was dried (Na₂SO₄), filtered and concentrated to an oil. Chromatography gave the pure (2RS,12bSR)-isomer which after concentration of the rich fractions was taken up in a minimum of ethanol, treated with ethanolic HCl, and ether was added to incipient cloudiness. After crystallization was complete there was collected 0.047 g of product with m.p. 266°–269° C.

Employing the procedure substantially as described in Example 8, but substituting for the quinolizine-2-one, ammonium acetate and sulfonyl chloride used therein, the Ar[2,3-a]quinolizin-2-ones, R³-ammonium acetates and R⁴-sulfonyl chlorides described in Table VI, there are prepared the N-(Ar[2,3-a]quinolizin-2β-yl)amines, also described in Table VI by the following reaction:

TABLE VI

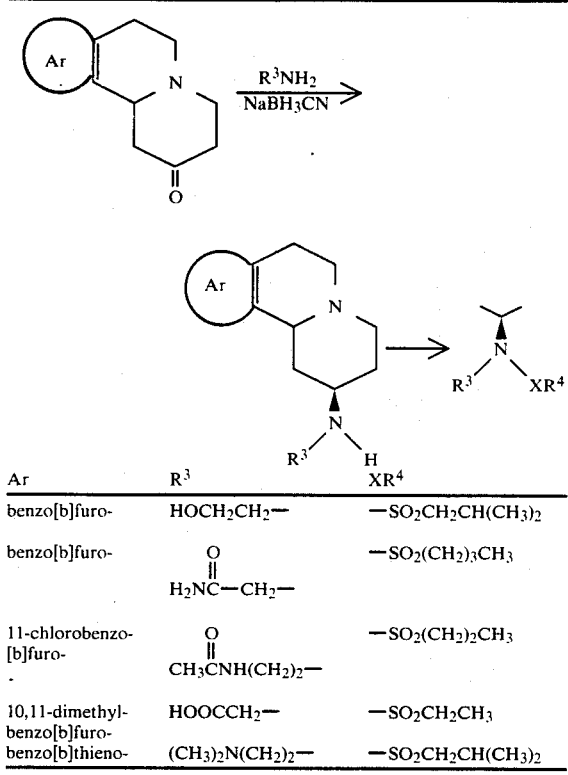

| Ar | R³ | XR⁴ |
|---|---|---|
| benzo[b]furo- | HOCH₂CH₂— | —SO₂CH₂CH(CH₃)₂ |
| benzo[b]furo- | H₂NC(O)—CH₂— | —SO₂(CH₂)₃CH₃ |
| 11-chlorobenzo[b]furo- | CH₃C(O)NH(CH₂)₂— | —SO₂(CH₂)₂CH₃ |
| 10,11-dimethyl-benzo[b]furo- | HOOCCH₂— | —SO₂CH₂CH₃ |
| benzo[b]thieno- | (CH₃)₂N(CH₂)₂— | —SO₂CH₂CH(CH₃)₂ |

EXAMPLE 9

(2SR,12bRS)-N-Acetyl-N-(1,3,4,6,7,12b-hexahydro-2H-benzo[b]furo[2,3-a]quinolizin-2-yl)-2-methylpropane sulfonamide To a solution of (2SR,12bRS)-N-(1,3,4,6,7,12b-hexahydro-2H-benzo[b]furo[2,3-a]quinolizin-2-yl)-2-methylpropane sulfonamide (362 mg; 1.0 mmol) in 20 mL of dry THF is added NaH (26 mg; 1.1 mmol). After the reaction is stirred 30 minutes at room temperature, a solution of acetyl chloride (86 mg; 1.1 mmol) in 5 mL of dry THF is added dropwise at 0° C. The reaction is warmed to room temperature and evaporated to dryness. The residue is extracted with ethyl acetate to which is then added ethanolic HCl, causing the hydrochloride salt of the product to crystallize.

By substituting for the acetyl chloride used in Example 9, approximately equimolar amounts of methyl formate, butanoyl chloride and heptanoyl chloride, there are produced, respectively the corresponding: (2SR,12bRS)-N-formyl, N-butanoyl and N-heptanoyl-N-(1,3,4,6,7,12b-hexahydro-2H-benzo[b]furo[2,3a]-quinolizin-2-yl)-2-methylpropane sulfonamide.

EXAMPLE 10

(2SR,12bRS)-N-(1,3,4,6,7,12b-Hexahydro-2H-benzo[b]furo[2,3-a]quinolizin-2-l)-1,3-propanesultam Step A: Preparation of (2SR,12bRS)-N-(1,3,4,6,7,12b-hexahydro-2H-benzo[b]furo[2,3-a]quinolizin-2-yl)-3-chloropropanesulfonamide.HCl To 0.300 g (1.24 mmol) of (2SR,12bRS)- and (2SR,12bSR)-N-(1,3,4,6,7,12b-hexahydro-2H-benzo[b]furo[2,3-a]quinolizin-2-amine dissolved in 3 ml of methylene chloride and cooled to 0° C. was added 0.150 g (1.49 mmol) of triethylamine and 0.242 g (1.37 mmol) of 3-chloropropanesulfonylchloride. The reaction was stirred 3 hours at 25° C., poured into 5% NaOH and washed with methylene chloride which is dried (Na₂SO₄), filtered and concentrated. The oil obtained was chromatographed (silica/10% MeOH/CHCl₃) giving 0.100 g of pure (2SR,12bSR)-isomer.

Step B: Preparation of (2SR,12bRS)-N-(1,3,4,6,7,12b-hexahydro-2H-benzo[b]furo[2,3-a]quinolizin-2-yl)-1,3-propanesultam.HCl The above sulfonamide (0.092 g, 0.24 mmol) was dissolved in 3 mL of dimethoxyethane (DME) and 0.055 g (0.48 mmol) of potassium t-butoxide was added. The reactants were heated at 60° C. for 2 hours and then poured into 5% NaOH and extracted with ether. The ether was washed with brine, dried (MgSO₄), filtered and concentrated to yield a crude product. Chromatography (silica; 5% MeOH/CHCl₃) gave 0.062 g of product. The product was taken up in ethanol, treated with ethanolic HCl and ether to incipient cloudiness. When crystallization was complete the product was collected and dried, m.p. 207°-210° C. (dec).

EXAMPLE 11

(2SR,12bRS)-N-(1,3,4,6,7,12b-Hexahydro-2H-benzo[b]furo[2,3-a]quinolizin-2-yl)oxazolin-2-one hydrochloride 0.25 hydrate Step A: Preparation of (2SR,12bRS)-N-(1,3,4,6,7,12b-Hexahydro-2H-benzo[b]furo[2,3-a]quinolizin-2-yl)-N-(2-hydroxyethyl)amine Ethanolamine (0.366 g, 6 mmol) and 0.241 g (1 mmol) of (2SR,12bRS)-1,3,4,6,7,12b-hexahydro-2H-benzo[b]furo[2,3-a]quinolizin-2-one were dissolved in 20 mL dry methanol, and ethanolic HCl added until the pH was 6.5. To this was added 0.038 g (0.6 mmol) of sodium cyanoborohydride and 3A molecular sieves. After stirring 18 hours, NH₃ saturated CHCl₃ was added until basic, and the solvent removed in vacuo. The residue was stirred in ethyl acetate, filtered and the solvent removed in vacuo. Purification by spinning disc chromatography (silica; NH₃ saturated CHCl₃) afforded 0.063 g (36%) of α-isomer and 0.112 g (64%) of β-isomer in 61% overall yield. The desired β-isomer was recrystallized from ether/pet. ether to yield white needles with m.p. 131°-132° C.

Step B: Preparation of (2SR,12bRS)-N-(1,3,4,6,7,12b-hexahydro-2H-benzo[b]furo[2,3-a]quinolizin-2-yl)-oxazolin-2-one hydrochloride 0.25 hydrate (2SR,12bRS)-N-(1,3,4,6,7,12b-Hexahydro-2H-benzo[b]furo-[2,3-a]-quinolizin-2-yl)-N-(2-hydroxyethyl)amine (0.71 g, 0.25 mmol) was placed in 5 ml dry toluene, and enough THF was added to make it homogeneous. To this was added dropwise 0.205 g (1.25 mmol) of carbonyl diimidazole in 2 ml dry toluene, and the reaction was refluxed 18 hours, after which time it was cooled and the solvent evaporated. Purification by spinning disc chromatography (silica; 5% (v/v) MeOH/CHCl₃) gave 0.062 g (0.2 mmol) of (2SR,12bRS)-N-(1,3,4,6,7,12b-hexahydro-2H-benzo[b]furo[2,3-a]quinolizin-2-yl)oxazolin-2-one in 79% yield. This was dissolved in ethyl acetate and ethanolic HCl was added dropwise to yield the hydrochloride 0.25 hydrate salt as a yellow solid, with m.p. 230° C. (dec).

EXAMPLE 12

(2SR,12bRS)-N-(1,3,4,6,7,12b-Hexahydro-2H-benzo[b]furo[2,3-a]quinolizin-2-yl)succinimide.

A mixture of (2SR,12bRS)-(1,3,4,6,7,12b-Hexahydro-2H-benzo[b]furo[2,3-a]quinolizin-2-yl)amine (80 mg; 0.33 mmol) and succinic anhydride (33 mg; 0.33 mmol) is heated under nitrogen at 130° C. for 2 hours. The residue is extracted into ethyl acetate which is washed with saturated NaHCO$_3$ solution. The organic phase is dried (Na$_2$SO$_4$), filtered and acidified with ethanolic HCl, causing the hydrochloride salt of the product to crystallize.

Employing maleic anhydride and glutaric anhydride in place of the succinic anhydride in Example 11, affords; respectively (2SR,12bRS)-N-(1,3,4,6,7,12b-hexahydro-2H-benzo[b]furo[2,3-a]-quinolizin-2-yl)maleimide; and (2SR,12bRS)-N-(1,3,4,6,7,12b-hexahydro-2H-benzo[b]furo[2,3-a]quinolizin-2-yl)glutarimide.

EXAMPLE 13

(2SR,10bRS)-N-(1,3,4,6,7,10b-Hexahydro-2H-thiazolo[4,5-a]quinolizin-2-yl)-N,N',N'-trimethylsulfamide, hydrochloride Step A: Preparation of Ethyl 4-oxo-pipecolinate, ethylene ketal.

A solution of ethyl 4-oxo-pipecolinate (17.1 g; 0.1 mole), ethylene glycol (6.8 g; 0.11 mole), and p-toluenesulfonic acid (0.5 g) in 250 mL of dry benzene is refluxed under Dean-Stark conditions for 18 hours. The benzene solution is washed with saturated aqueous NaHCO$_3$ solution, dried (Na$_2$SO$_4$, and evaporated to afford the desired product.

Step B: Preparation of Ethyl N-(3-Ethoxycarbonylpropyl)-4-oxo-pipecolinate, ethylene ketal.

A mixture of ethyl 4-oxo-pipecolinate, ethylene ketal (12.9 g; 60 mmol), ethyl 4-bromobutyrte (12.9 g; 66 mmol), and K$_2$CO$_3$ (12.0 g; 86 mmol) in 250 mL of toluene is heated at 80° C. for 4 hours. The solid is then filtered off, and the filtrate is concentrated. Distillation of the residue affords the product.

Step C: Preparation of 1,3,4,6,7,8,9,9a-Octahydro-2H-quinolizin-1,8-dione-2-carboxylic acid, ethyl ester, 8-ethylene ketal.

Ethyl N-(3-ethoxycarbonylpropyl)-4-oxo-pipecolinate, ethylene ketal (3.29 g; 10 mmol) is added to a stirred suspension of NaH (0.58 g of a 50% dispersion in oil; 12 mmol) in 5 mL of dry toluene. The reaction is then refluxed for 2 hours. Water is added, followed by acetic acid until the reaction is neutral. The organic fraction is separated, dried (Na$_2$SO$_4$), and concentrated to yield the crude product.

Step D: Preparation of 1,3,4,6,7,8,9,9a-Octahydro-2H-quinolizin-1.8-dione. 8-ethylenen ketal.

A mixture of 1,3,4,6,7,8,9,9a-octahydro-2H-quinolizin-1,8-dione-2-carboxylic acid, ethyl ester, 8-ethylene ketal (2.83 g; 10 mmol), LiCl (0.84 g; 20 mmol), and water (0.36 g; 20 mmol) in 25 mL of DMSO is heated to 180° C. for 2 hours. After the reaction is cooled to room temperature, it is partitioned between ethyl acetate and water. The organic extracts are separated, dried (Na$_2$SO$_4$), and concentrated. The residue is chromatographed over silica gel to give the product.

Step E: Preparation of 2-Bromo-1,3,4,6,7,8,9,9a-Octahydro-2H-quinolizin-1,8-dione, 8-ethylene ketal.

To a solution of 1,3,4,6,7,8,9,9a-octahydro-2H-quinolizin-1,8-dione, 8-ethylene ketal (2.1 g; 10 mmol) in 20 mL of dry methylene chloride is added dropwise a solution of benzyltrimethylammonium bromide perbromide (3.9 g; 10 mmol) in 10 mL of methylene chloride at 0° C. After 2 hours, the reaction mixture is washed three time with water. The organic phase is dried (Na$_2$SO$_4$) and concentrated in vacuo to yield the crude product which is used without further purification.

Step F: Preparation of 1,3,4,6,7,10b-Hexahydro-2H-thiazolo[4,5-a]quinolizin-2-one, ethylene ketal.

A solution of 2-bromo-1,3,4,6,7,8,9,9a-octahydro-2H-quinolizin-1,8-dione, 8-ethylene ketal (4.3 g; 15 mmol) and thioformamide (1,8 g; 30 mmol) in 10 mL of DMF is stirred with 2.0 g of 3A-molecular sieves at 50° C. for 8 hours. After the solid is filtered, the filtrate is poured into water, causing the product to crystallize.

Step G: Preparation of 1,3,4,6,7,10b-Hexahydro-2H-thiazolo [4,5-a]quinolizin-2-one 1,3,4,6,7,10b-Hexahydro-2H-thiazolo[4,5-a]-quinolizin-2-one, ethylene ketal (1.0 g) is dissolved in 25 mL of acetone. 6N HCl (2.0 mL) is added, and the reaction is stirred at room temperature for 4 hours. The acetone is removed in vacuo, and the aqueous fraction is made basic with K$_2$CO$_3$. This mixture is extracted with methylene chloride (3×10 mL). The organic extracts are then dried (Na$_2$SO$_4$) and concentrated to afford the product.

Following the procedures substantially as described in Example 1, Steps F and G but substituting for the quinolizin-2-one used therein, an equimolar amount of the quinolizin-2-one from Step G of this Example 13, there are produced in sequence: (2RS,10bSR)-N-(1,3,4,6,7,10b-hexahydro-2H-thiazolo[4,5-a]quinolizin-2-yl)-N-methylamine; and (2RS,10bSR)-N-(1,3,4,6,7,10b-hexahydro-2H-thiazolo[4,5-a]quinolizin-2-yl)-N,N',N'-trimethylsulfamide, hydrochloride.

Similarly prepared are those compounds wherein Ar is thiazolo and —X—R$^4$ are —SO$_2$CH$_2$CH$_2$OH, —SO$_2$CH$_2$CH$_3$, and —SO$_2$(CH$_2$)$_3$OH.

EXAMPLE 14

(2SR,10bRS)-N-(1,3,4,6,7,10b-Hexahydro-2H-imidazolo[4,5-a]quinolizin-2-yl)-N,N',N'-trimethylsulfamide, hydrochloride Step A: Preparation of (10bRS)-1,3,4,6,7,10b-hexahydro-2H-imidazo[4,5-a]quinolizin-2-one, ethylene ketal.

Formamidine acetate (3.1 g; 30 mmol) is added to a solution of 2-bromo-1,3,4,6,7,8,9,9a-octahydro-2H-quinolizin-1,8-dione, 8-ethylene ketal (4.3 g; 15 mmol) in 15 mL of ethanol. The reaction is refluxed for 3 hours and then concentrated. The residue is partitioned between ethyl acetate and saturated NaHCO$_3$. The organic fraction is dried (Na$_2$SO$_4$) and evaporated to yield the desired product, after chromatography over silica gel.

Step B: Preparation of (10bRS)-1,3,4,6,7,10b-Hexahydro-2H-imidazo[4,5-a]quinolizin-2-one.

(10bRS)-1,3,4,6,7,10b-Hexahydro-2H-imidazo[4,5-a]quinolizin-2-one, ethylene ketal (2.0 g) is dissolved in 25 mL of a mixture of acetone-6N HCl (10:1) and stirred at room temperature for 6 hours. The acetone is removed in vacuo, and the aqueous fraction is made basic with K$_2$CO$_3$. This mixture is extracted with methylene chloride. The organic extracts are then dried (Na$_2$SO$_4$) and concentrated to afford the product.

Following the procedures substantially as described in Example 1, Steps F and G but substituting for the quinolizin-2-one used therein, an equimolar amount of the quinolizin-2-one from Step B of this Example 14 there are produced in sequence:
(2SR,10bRS)-N-(1,3,4,6,7,10b-hexahydro-2H-imidazolo[4,5-a]quinolizin-2-yl)-N-methylamine; and
(2SR,10bRS)-N-(1,3,4,6,7,10b-hexahydro-2H-imidazolo[4,5-a]quinolizin-2-yl)-N,N',N'-trimethylsulfamide, hydrochloride.

Similarly prepared are those compounds wherein Ar is imidazo and —X—$R^4$ are —$SO_2(CH_2)_2OH$—, $SO_2(CH_2)$ and $SO^{-d\ 2}CH_2CH_3$.

EXAMPLE 15

(2SR,10bRS)-N-(1,3,4,6,7,10b-Hexahydro-2H-pyrazolo[3,4-a]quinolizin-2-yl)-N,N',N'-trimethylsulfamide, hydrochloride Step A: Preparation of (10SR)-1,3,4,6,7,10-Hexahydro-2H-pyrazolo[3,4-a]quinolizin-2-one, ethylene ketal.

(9aSR)-1,3,4,6,7,8,9,9a-Octahydro-2H-quinolizin-1,8-dione, 8-ethylene ketal (4.2 g; 20 mmol) and DMF-dimethyl acetal (2.86 g; 24 mmol) are heated at 100° C. under nitrogen for 16 hours. The dark residue is then dissolved in 5 mL of ethanol and treated with anhydrous hydrazine (1.28 g; 40 mmol). The reaction is stirred at room temperature for 18 hours. The solvent is evaporated, and the residue is chromatographed over silica gel, eluting with 5% MeOH/ $CHCl_3$ saturated with ammonia to yield the product.

Step B: Preparation of (10SR)-1,2,3,4,6,7,10-Hexahydro-2H-pyrazolo[3,4-a]quinolizin-2-one 1,2,3,4,6,7,10-Hexahydro-2H-pyrazolo[3,4-a]-aquinolizin-2-one, ethylene ketal (1.0 g) is dissolved in 25 mL of a mixture of acetone-6N HCl (10:1) and stirred at room temperature for 5 hours. The acetone is removed in vacuo, and the aqueous fraction is made basic with $K_2CO_3$. This mixture is extracted with methylene chloride. The organic extracts are then dried ($Na_2SO_4$) and concentrated to afford the product.

Following the procedure substantially as described in Example 1, Steps F and G but substituting for the quinolizin-2-one used therein, an equimolecular amount of the quinolizin-2-one from Step B of this Example 15, there are produced in sequence.
(2SR,10bRS)-N-(1,3,4,6,7,10b-hexahydro-2H-pyrazolo[3,4-a]quinolizin-2-yl)-N-methylamine; and
(2SR,10bRS)-N-(1,3,4,6,7,10b-hexahydro-2H-pyrazolo[3,4-a]quinolizin-2-yl)-N,N',N'-trimethylsulfonamide.

Similarly prepared are those compounds wherein Ar is pyrazolo and —$XR^4$ are —$SO_2(CH_2)_2OH$, —$SO_2(CH_2)_3OH$ and —$SO_2CH_2CH_3$.

EXAMPLE 16

(2SR,11bRS)-N-(1,3,4,6,7,11b-Hexahydro-2H-pyrido[2,3-a]quinolizin-2-yl)-N,N',N'-trimethylsulfamide, hydrochloride Step A: Preparation of 2-(2-(1,3-Dioxolan-2-yl)ethyl)-1,3,4,6,7,8,9,9a-Octahydro-2H-quinolizin-1,8-dione-2-carboxylic acid, ethyl ester. 8-ethylene ketal.

1,3,4,6,7,8,9,9a-Octahydro-2H-quinolizin-1,8-dione-2-carboxylic acid, ethyl ester, 8-ethylene ketal (5.7 g; 20 mmol) is added in small portions to a stirred suspension of NaH (0.48 g; 20 mmol) in 50 mL of toluene/DMF (1:1). After 15 minutes 2-(2-bromoethyl)-1,3-dioxolane is added in one portion, and the reaction is refluxed for 4 hours. The mixture is cooled and partitioned between water and ethyl acetate. The organic layer is washed well with water, dried ($Na_2SO_4$), and concentrated. The residue is chromatographed over silica gel to afford the product.

Step B: Preparation of 2-(2-(1,3-Dioxolan-2-yl)ethyl)-1,3,4,6,7,8,9,9a-octahydro-2H-quinolizin-1,8-dione, 8-ethylene ketal.

A mixture of 2-(2-(1,3-dioxolan-2-yl)ethyl)-1,3,4,6,7,8,9,9a-octahydro-2H-quinolizin-1,8-dione-2-carboxylic acid, ethyl ester, 8-ethylene ketal (1.9 g; 5 mmol), LiCl (0.42 g; 10 mmol), water (0.18 g; 10 mmol), and 20 mL DMSO is heated at 180° C. for 2 hours. The reaction is then poured into 100 mL of water and extracted with ethyl acetate. The organic fraction is washed well with water, dried ($Na_2SO_4$), and concentrated. The residue is chromatographed over silica gel to yield the desired product.

Step C: Preparation of (2SR,11bRS)-1,3,4,6,7,11b-Hexahydro-2H-pyrido[2,3-a]quinolizin-2-one, ethylene ketal.

A Solution of 2-(2-(1,3-dioxolan-2-yl)ethyl)-1,3,4,6,7,8,9,9a-octahydro-2H-quinolizin-1,8-dione, 8-ethylene ketal (1.5 g; 5 mmol) and hydroxylamine hydrochloride (0.7 g; 10 mmol) in 25 mL absolute ethanol is refluxed for 2 hours. The solvent is evaporated, and the residue is chromatographed over silica gel to give the product.

Step D: Preparation of (2SR,11bRS)-1,3,4,6,7,11b-Hexahydro-2H-pyrido[2,3-a]quinolizin-2-one.

A Solution of 1,3,4,6,7,11b-hexahydro-2H-pyrido[2,3-a]quinolizin-2-one, ethylene ketal (2.0 g) in 50 mL of acetone/6N HCl (10:1) is stirred at room temperature for 3 hours. The acetone is removed in vacuo, and the aqueous fraction is made basic with $K_2CO_3$. The resulting mixture is extracted with methylene chloride, which is then dried ($Na_2SO_4$) and concentrated to afford the product.

Employing the procedures substantially as described in Example 1, Steps F and G but substituting for the quinolizin-2-one used therein, an equimolar amount of the quinolizin-2-one from Step D of this Example 16, there are produced in sequence:
(2SR,11bRS)-N-(1,3,4,6,7,11b-hexahydro-2H-pyrido[2,3-a]quinolizin-2-yl)-N-methylamine; and
(2SR,11bRS)-N-(1,3,4,6,7,11b-hexahydro-2H-pyrido[2,3-a]quinolizin-2-yl)-N,N',N'-trimethylsulfamide, hydrochloride.

Similarly prepared are those compounds wherein Ar is pyrido and $XR^4$ is —$SO_2(CH_2)_2OH$, —$SO_2(CH_2)_3OH$ and $SO_2CH_2CH_3$.

EXAMPLE 17

(2R,12bS)-N-(1,3,4,6,7,12b-hexahydro-2H-benzo[b]furo[2,3-a]quinolizin-2-yl)-N-(2((methylsulfonyl)amino)ethyl)-methanesulfonamide monohydrochloride Step A: The preparation of (2R,12bS)-N-(1,3,4,6,7,12b-hexahydro-2H-benzo[b]furo[2,3-a]quinolizin-2-yl)-ethylenediamine To a solution of (12bS)-1,3,4,6,7,12b-hexahydro-2H-benzo[b]furo[2,3-a]quinolizin-2-one (2.41 g, 10 mmol) in 50 ml of THF was added 1.7 ml of 6N HCl solution. After stirring 1 hour the white precipitate was filtered and dried to give 2.7 g of product which was suspended in 200 ml of isopropanol along with 11 g of 4A molecular sieves and 2.95 g (49 mmol) of ethylenediamine was added. The reaction was heated for 18 hour, cooled to 0° C. and then 1.05 g (27.6 mmol) of sodium borohydride was added. The temperature was raised to 50° C., stirred for 1 hour and cooled, filtered and concentrated. The residue was diluted with 80 ml of 10% NaOH solution and extracted with ethyl acetate. The organic layer was dried, filtered and concentrated to give 2.64 g of the crude product. This was chromatographed (SiO$_2$, 20% CH$_3$OH/NH$_3$ saturated chloroform) to give 2.14 g of pure product.

Step B: The preparation of (2R,12bS)-N-(1,3,4,6,7,12b-hexahydro-2H-benzo[b]furo[2,3-a]quinolizin-2-yl)-N-(2-((methylsulfonyl)amino)ethyl)-methanesulfonamide monohydrochloride To a solution of (2R,12bS)-N-(1,3,4,6,7,12b-hexahydro-2H-benzo[b]furo[2,3-a]quinolizin-2-yl)ethylenediamine (2.14 g, 7.5 mmol) in 70 ml of methylene chloride was added 1.67 g (16.5 mmol) of triethylamine followed by 1.88 g (16.5 mmol) of methanesulfonyl chloride. After 30 minutes an additional 8 mmol of methanesulfonyl chloride was added. After 2 hours the reaction was diluted with 70 ml of saturated sodium bicarbonate solution and this was washed with methylene chloride. The organic layer was dried, filtered and concentrated to give the crude product. This was chromatographed (SiO$_2$, 5% CH$_3$OH/NH$_3$ saturated chloroform) to yield 1.15 g of product. The hydrochloride salt has m.p. 219°–221° C. $[\alpha]_D$—22.8° (CH$_3$OH, c=0.001)

EXAMPLE 18

(2R,12bS)-N-(1,3,4,6,7,12b-hexahydro-2H-benzo[b]furo[2,3-a]quinolizin-2-yl)-N-(2(methyl(methylsulfonyl)amino)ethyl)-methanesulfonamide monohydrochloride To a vigorously stirring solution of 100 mg (0.21 mmol) of (2R,12bS)-N-(1,3,4,6,7,12b-hexahydro-2H-benzo[b]furo[2,3-a]quinolizin-2-yl)-N-(2((methylsulfonyl)amino)ethyl)-methanesulfonamide monohydrochloride in a mixture of 5 ml of toluene and 5 ml of 40% NaOH solution was added 107 mg (0.31 mmol) of tetra-n-butyl-ammonium sulfate followed by 45 mg (0.31 mmol) of methyl iodide. After 30 minutes the reaction was worked up by diluting with water and washing with methylene chloride. The organic layer was dried, filtered and concentrated to give the crude product. This was chromatographed (SiO$_2$, 5%CH$_3$OH/NH$_3$ saturated chloroform) to yield 70 mg of product. The hydrochloride has mp=156°–159° C. $[\alpha]_D$—14° (CH$_3$OH,c=0.001).

EXAMPLE 19

(2SR,12bRS)-N-(1,3,4,6,7,12b-hexahydro-2H-benzo[b]thieno[2,3-a]quinolizin-2-yl)-N-(2((methylsulfonyl)amino)ethyl)-methanesulfonamide monohydrochloride Step A: The preparation of (2RS,12bSR)-N-(1,3,4,6,7,12b-hexahydro-2H-benzo[b]thieno[2,3-a]quinolizin-2-yl)ethylenediamine To a solution of (12bRS)-1,3,4,6,7,12b-hexahydro-2H-benzo[b]thieno[2,3-a]quinolizin-2-one (257 mg, 1.0 mmol) in 40 ml of THF was added 0.17 ml of 6N HCl solution. After stirring 1 hour the white precipitate was filtered and dried to give 290 mg of ketone hydrochloride which was suspended in 30 ml of isopropanol along with 1.1 g of 4A molecular sieves and 295 mg (4.9 mmol) of ethylenediamine was added. The reaction was heated for 18 hours, cooled to 0° C. and then 105 mg (2.76 mmol) of sodium borohydride was added. The temperature was raised to 50° C., stirred for 1 hour and cooled, filtered and concentrated. The residue was diluted with 30 ml of 10% NaOH solution and extracted with ethyl acetate. The organic layer was dried, filtered and concentrated to give 304 mg of the crude product. This was chromatographed (SiO$_2$, 20% CH$_3$OH/NH$_3$ saturated chloroform) to give 295 mg of pure product.

Step B: The preparation of (2SR,12bRS)-N-(1,3,4,6,7,12b-hexahydro-2H-benzo[b]thieno[2,3-a]quinolizin-2-yl)-N-(2((methylsulfonyl)amino)ethyl)-methanesulfonamide monohydrochloride To a solution of (2SR,12bRS)-N-(1,3,4,6,7,12b-hexahydro-2H-benzo[b]thieno[2,3-a]quinolizin-2-yl)ethylenediamine (295 mg, 0.98 mmol) in 15 ml of methylene chloride was added 218 mg (2.16 mmol) of triethylamine followed by 246 mg (2.16 mmol) of methanesulfonyl chloride. After 30 minutes an additional 8 mmol of methanesulfonyl chloride was added. After 2 hours the reaction was diluted with 30 ml of saturated sodium bicarbonate solution and this was washed with methylene chloride. The organic layer was dried, filtered and concentrated to give the crude product. This was chromatographed (SiO$_2$, 5% CH$_3$OH/NH$_3$ saturated chloroform) to yield 135 mg of product. The hydrochloride salt has mp=256°–258° C.

EXAMPLE 20

(2R,12bS)-N-(1,3,4,6,7,12b-hexahydro-2H-benzo[b]furo[2,3-a]quinolizin-2-yl)-N-(2-((methylsulfonyl)amino)ethyl)amine To a solution of (2SR,12bRS)-N-(1,3,4,6,7,12b-hexahydro-2H-benzo[b]furo[2,3-a]quinolizin-2-yl)ethylenediamine (1.2 g, 4.2 mmol) in 50 ml of methylene chloride and 25 ml of water containing 620 mg of potassium carbonate was added 800 mg (4.5 mmol) of methanesulfonic anhydride. This was stirred at room temperature for 2 hours and then diluted with water and extracted with methylene chloride. The organic layer was dried, filtered and concentrated to give the crude product. This was chromatographed to give 1.05 g of product. The dihydrochloride has m.p. 276°–278° C.(dec).

EXAMPLE 21

(2R,12bS)-N-(1,3,4,6,7,12b-hexahydro-2H-benzo[b]furo[2,3-a]quinolizin-2-yl)-N-(2-((methylsulfonyl)amino)ethyl)-propanesulfonamide monohydrochloride To a solution of (2R, 12bS)-N-(1,3,4,6,7,12b-hexahydro-2H-benzo[b]furo[2,3-a]quinolizin-2-yl)-N-2-((methylsulfonyl)amino)ethyl)amine (500 ) mg, 1.38 mmol) in 15 ml of methylene chloride at 0° C. was added triethylamine (348 mg, 3.44 mmol) followed by propanesulfonyl chloride. This was stirred at 0° C. for 1 hour and then warmed to room temperature and stirred overnight, after an additional 1 equivalent of propanesulfonyl chloride was added, after 24 hours at room temperature the reaction was diluted with water and washed with methylene chloride. The organic layer was dried, filtered and concentrated to give the crude product. This was chromatographed (SiO$_2$, 5% CH$_3$OH,NH$_3$/chloroform) to give 145 mg of the title compound. the hydrochloride salt has mp=147°–150° C.

EXAMPLE 22

(2SR,12bSR)-N-(2-((1,3,4,6,7,12b-hexahydro-2H-benzo[b]furo[2,3-a]quinolizin-2-yl)(methylsulfonyl)amino)ethyl)acetamide Step A: The preparation of (2RS,12bSR)-N-(1,3,4,6,7,12b-hexahydro-2H-benzo[b]furo[2,3-a]quinolizin-2-yl)-N-(2-aminoethyl)acetamide To a solution of (12bRS)-1,3,4,6,7,12b-hexahydro-2H-benzo[b]furo[2,3-a]quinolizin-2-one (2.41 g, 10 mmol) in 70 ml of benzene was added 2.04 g (20 mmol) of N-acetyl ethylenediamine and 170 mg (0.89 mmol) of p-toluenesulfonic acid monohydrate. This was heated for 18 hours with removal of water. The reaction was cooled and concentrated to dryness, diluted with 150 ml of ethanol and 1.0 g (26.3 mmol) of sodium borohydride added. This was stirred 2 hours at room temperature and then diluted with 50 ml of water, stirred 1 hour, concentrated and washed with methylene chloride. The organic layer was dried, filtered and concentrated to give the crude product. This was chromatographed to give 1.65 g of product.

STEP B: The preparation of (2SR,12bSR)-N-(2-((1,3,4,6,7,12b-hexahydro-2H-benzo[b]furo[2,3-a]quinolizine-2-yl)(methylsulfonyl)amino)ethyl)acetamide To a solution of (2RS,12bSR)-N-(1,3,4,6,7,12b-hexahydro-2H-benzo[b]furo[2,3-a]quinolizin-2-yl)-N 2-aminoethyl)acetamide (1.65 g, 5.05 mmol) in 60 ml of methylene chloride was added 660 mg (6.53 mmol) of triethylamine and 747 mg (6.55 mmol) of methanesulfonyl chloride. After 2 hours the reaction was poured into 100 ml of saturated sodium bicarbonate solution and extracted into methylene chloride. The organic layer was dried, filtered and concentrated to give the crude product. This was chromatographed (SiO$_2$, 1% CH$_3$OH/NH$_3$ saturated chloroform) to give 1.1 g of product. The hydrochloride salt has m.p. = 192°–194° C.

EXAMPLE 23

2S R,3RS,12bRS)-N-(1,3,4,6,7,12b-hexahydro-3-methyl-(2H-benzo[b]furo[2,3-a]quinolizin-2-yl)-N-(2-((methylsulfonyl)amino)ethyl)methanesulfonamide and (2RS,3RS,12bRS)-N-(1,3,4,6,7,12b-hexahydro-3-methyl-2H-benzo[b]furo[2,3-a]quinolizin-2-yl)-N-(2-((methylsulfonyl)amino)ethyl)methanesulfonamide Step A: Preparation of (2SR,3RS,12bRS)-N-(1,3,4,6,7,12b-hexahydro-3-methyl-2H-benzo[b]furo[2,3-a]quinolizin-2-yl)ethylenediamine and (2RS,3RS,12bRS)-N-(1,3,4,6,7,12b-hexahydro-3-methyl-2H-benzo[b]furo[2,3-a]quinolizin-2-yl)ethylenediamine To a solution of (3RS,12bRS)-1,3,4,6,7,12b-hexahydro-3-methyl-benzo[b]furo[2,3-a]quinolizin-2-one (0.510 g, 2.0 mmol) in 13 ml of THF was added 0.35 ml (2.1 mmol) of 6N HCl. The white precipitate was collected and dried in vacuo, then suspended in 40 ml isopropanol. To the suspension was added 0.67 ml (10.0 mmol) of ethylenediamine and 2.5 g of 4A sieves, after which the reaction was heated at reflux for 17 hours. After cooling to 0° C., 0.30 g (8.0 mmol) of sodium borohydride was added and the reaction heated at 60° C. for 3 hours. The reaction was quenched with 10 ml of water, stirred 1 hour more at room temperature, then filtered and extracted with CH$_2$Cl$_2$. The combined organic layers were dried (Na$_2$SO$_4$), filtered and concentrated to an oil which was chromatographed (silica, 10% MeOH/CHCl$_3$) to give 0.461 g (77%) of a mixture of diastereomeric products (2SR,3RS,12bRS)-N-(1,3,4,6,7,12b-hexahydro-3-methyl-2H-benzo[b]furo[2,3-a]quinolizin-2-yl)ethlenediamine ethlenediamine and (2RS,3RS,12bRS)-N-(1,3,4,6,7,12b-hexahydro-3-methyl-2H-benzo[b]furo[2,3-a]quinolizin-2-yl)ethylenediamine in a ratio of about 35:65. (LRMS: m/z 299).

Step B: Preparation of (2SR,3RS,12bRS)-N-(1,3,4,6,7,12b-hexahydro-3-methyl-2H-benzo[b]furo[2,3-a]quinolizin-2-yl)-N-(2-((methylsulfonyl)amino)ethyl)methanesulfonamide HCl and (2RS,3RS,12bRS)-N-(1,3,4,6,7,12b-hexahydro-3-methyl-2H-benzo[b]furo[2,3-a]quinolizin-2-yl)-N-(2-((methylsulfonyl)amino)ethyl)methanesulfonamide HCl To a solution of 0.408, (1.36 mmol) of the mixture of diastereomeric products from above in 13 ml CH$_2$Cl$_2$ was added 0.47 ml (3.40 mmol) of triethylamine, followed by 0.26 ml (3.40 mmol) of methanesulfonylchloride. After stirring 1 hour at room temperature, saturated aqueous NaHCO$_3$ was added and the mixture was extracted with CH$_2$Cl$_2$. The combined organic layers were dried (Na$_2$SO$_4$), filtered and concentrated to provide a light yellow foam. Flash column chromatography (silica, 3% CH$_3$OH/ethyl acetate) separated the diastereomeric products to provide 0.190 g of (2SR,3RS,12bRS)-N-(1,3,4,6,7,12b-hexahydro-3-methyl-2H-benzo[b]furo[2,3-a]quinolizin-2-yl)-N-(2-((methylsulfonyl)amino)ethyl)methanesulfonamide, isolated as the HCl salt, m.p. 239°–243° C., and 0.350 g of (2RS,3RS,12bRS)-N-(1,3,4,6,7,12b-hexahydro-3-methyl-2H-benzo[b]furo[2,3-a]quinolizin-2-yl)-N-(2-((methylsulfonyl)amino)ethyl)methanesulfonamide, isolated as the HCl salt, m.p. 258°–263° C.

EXAMPLE 24

(2SR,12bRS)-N-(1,3,4,6,7,12b-hexahydro-2H-benzo[b]furo[2,3-a]quinolizin-2-yl)-N-(2-((ethylsulfonyl)amino)ethyl)ethanesulfonamide To a solution of 0.285 g (1.0 mmol) of 2SR,12bRS)-N-(1,3,4,6,7,12b-hexahydro-2H-benzo[b]furo[2,3-a]quinolizin-2-yl)ethylenediamine and (2.5 mmol) of triethylamine in 10 ml CH$_2$Cl$_2$ was added 0.25 ml (2.5 mmol) of ethanesulfonyl chloride. After stirring 1 hour at room temperature, TLC showed the reaction was only partially complete. A further 0.14 ml (1.0 mmol) of triethylamine and 0.1 ml (1.0 mmol) of ethanesulfonyl chloride was added. After a further 1¼ hour at room temperature, the mixture was washed with aqueous saturated NaHCO$_3$ solution and further extracted with CH$_2$Cl$_2$. The combined organic layers were dried (Na$_2$SO$_4$), filtered and concentrated to a brown foam which was chromatographed (silica, 6% CH$_3$OH/ethyl acetate) to give 0.247 g (53%) of (2SR,12bRS)-N-(1,3,4,6,7,12b-hexahydro-2H-benzo[b]furo[2,3-a]quinolizin-2-yl)-N-(2-((ethylsulfonyl)amino)ethyl)ethanesulfonamide, which was converted to the HCl salt, m.p. 211° C. (dec).

EXAMPLE 25

Preparation of (2SR,12bRS)-N-(1,3,4,6,7,12b-hexahydro-2H-benzo[b]furo[2,3-a]quinolizin-2-yl)-N-(2-((methylsulfonyl)amino)ethyl)ethanesulfonamide To a solution of 0.727 g (2.0 mmol) of (2SR,12bRS)-N-(1,3,4,6,7,12b-hexahydro-2H-benzo[b]furo[2,3-a]quinolizin-2-yl)-N-(2-((methylsulfonyl)amino)ethyl)amine in 20 ml CH$_2$Cl$_{12}$ at 0° C. was added 0.33 ml (2.4 mmol) of triethylamine. and 0.24 ml (2.4 mmol) of ethanesulfonyl chloride. After stirring 15 minutes at 0° C. and 2 hours further at room temperature, the mixture was washed with aqueous saturated NaHCO$_3$ solution and further extracted with CH$_2$Cl$_2$. The combined organic layers were dried (Na₂SO₄), filtered and concentrated to a foam which was chromatographed (silica, 5% CH₃OH/ethyl acetate) to give 0.432 g (47%) of product. A mixture of the free base in CH₃₀OH-ethylacetate was acidified with ethanolic HCl to afford the hydrochloride salt, 2/3 ethyl acetate solvate m.p. 174°-178° C.

Employing the procedure substantially as described in Example 25 but substituting for the ethanesulfonyl chloride the amounts as indicated of the compounds R⁴—X—Cl, there are produced the R⁴X) amines described in Table VII, in accordance with the following reaction:

shell capsules of a suitable size at a fill weight of 100 mg per capsule.

EXAMPLE 27

| Ingredient | Mg/Capsule |
|---|---|
| (2SR,12bRS)-N—(1,3,4,6,7,12b-Hexahydro-2H—benzo[b]furo[2,3-a]-quinolizin-2-yl)-N—methyl-2-hydroxy-ethanesulfonamide.HCl | 6 |
| starch | 87 |
| magnesium stearate | 7 |

TABLE VII

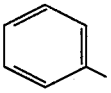

| R⁴— | X | EQUIVS. of R⁴—XCl | REACTION TIME/TEMP | YIELD | SALT MP (°C.) |
|---|---|---|---|---|---|
| 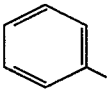 | —SO₂— | 1.5 | 1 hour/0° C. + 4 hours/RT | 62% | .HCl.H₂O, 156-162° |
| 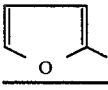 | —CO— | 1.2 | ½ hour/0° C. | 81% | .HCl, 253-256° (DEC) |
| (CH₃)₂N— | —CO— | 1.8 | ½ hour/0° C. + 90 hours/RT | 64% | .HCl.½H₂O, 185-187° C. |
| (furyl) | —CO— | 1.2 | ½ hour/0° C. + 1½ hours/RT | 57% | .HCl, 235-237° (DEC) |

EXAMPLE 26

Pharmaceutical Formulation

| Ingredient | Mg/Capsule |
|---|---|
| (2SR,12bRS)-N—(1,3,4,6,7,12b-Hexahydro-2H—benzo[b]furo[2,3-a]-quinolizin-2-yl)-N,N',N'—trimethyl-sulfamide.HCl | 6 |
| starch | 87 |
| magnesium stearate | 7 |

The active ingredient, starch and magnesium stearate are blended together. The mixture is used to fill hard

What is claimed is:

1. A compound of structural formula:

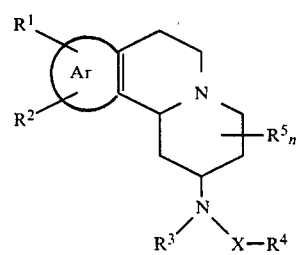

or a pharmaceutically acceptable salt thereof wherein

Ar represents an aromatic heterocycle selected from R$^1$, R$^2$-benzo[b]furo-, R$^1$, R$^2$-benzo[b]thieno-, thieno- and furo-;

R$^1$ and R$^2$ are independently:
(1) hydrogen,
(2) halo,
(3) hydroxy,
(4) C$_{1-3}$ alkoxy, or
(5) C$_{1-6}$ alkyl;

R$^3$ is
(1) hydrogen,
(2)

wherein R is hydrogen or C$_{1-3}$ alkyl,
(3) C$_{1-6}$ alkyl, either unsubstituted or substituted with one or more of;
(a) hydroxy,
(b) carboxy,
(c) C$_{1-3}$ alkoxycarbonyl,
(d) halo,
(e) C$_{1-3}$ alkoxy,
(f) —CONR$^6$R$^7$, wherein R$^6$ and R$^7$ are the same or different and are hydrogen or C$_{1-5}$alkyl, or joined together directly to form a pyrrolidino or piperidino ring or through a heteroatom to form a morpholino, piperazino or N-C$_{1-3}$ alkylpiperazino heterocycle, or
(g) —NR$^6$R$^7$;
(h)

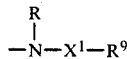

wherein X$^1$ is

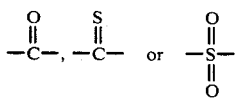

and R$^9$ is
(i) C$_{1-3}$ alkoxy,
(ii) C$_{1-3}$ alkyl, or
(iii) NR$^6$R$^7$;

X is

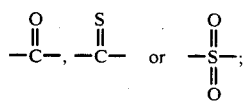

and R$^4$ is
(1) —OR$^8$, wherein R$^8$ is hydrogen or C$_{1-6}$ alkyl, either unsubstituted or substituted with one or more of;
(a) OR, or
(b) —NRCOR;
(2) —N(R$^8$)$_2$,
(3) —CO$^2$R$^8$,
(4) —CONR$^6$R$^7$,
(5) C$_{1-6}$ alkyl, either unsubstituted or substituted with (a) OR8
(b) halo,
(c) CO$_2$R$^8$
(d) CONR$^6$R$^7$,
(6) C$_{2-5}$ alkenyl,
(7) C$_{2-5}$ alkynyl,
(8) C$_{3-6}$ cycloalkyl,
(9) 5 or 6-membered heterocycle selected from imidazo, thiazolo, oxazolo, furamyl piperidino, piperzino, pyridino and pyrazino, or phenyl or napthyl, either unsubstituted or substituted with one or more of;
(a) halo, or
(b) OR, or
(c) C$_{1-3}$ alkyl;

R$^5$ is independently
(1) C$_{1-6}$ alkyl, either unsubstituted or substituted with one or more of
(a) —OR$^8$,
(b) —NR$^8$COR$^8$, or
(c) —CO$_2$R$^8$,
(2) —CO$_2$R$^8$, or
(3) —CONR$^6$R$^7$;

n is 0, 1, 2 or 3; and

R$^3$ and R$^4$ taken together form a 2-oxazolidinon-1-yl or succinimidoyl group or;

R$^3$ and R$^5$ or R$^4$ and R$^5$, if R$^5$ is in the 1- or 3-position and both are alkyl, can be joined together to form a 5- or 6-membered ring.

2. The compound of claim 1 or a pharmaceutically acceptable salt thereof wherein Ar is R$^1$,R$^2$-benzo[b]furo- or R$^1$,R$^2$-benzo[b]thieno-; R$^1$ and R$^2$ are hydrogen or halo; R$^3$ is C$_{1-6}$ alkyl, X is —SO$_2$— and R$^4$ is C$_{1-6}$ alkyl, di(C$_{1-3}$ alkyl)amino, halo-C$_{1-6}$ alkyl, hydroxy-C$_{1-6}$ alkyl C$_{2-5}$ alkenyl, C$_{6-10}$carbocyclic aryl, 5 or 6-membered heterocycle, —CO$_2$R$^8$, —C$_{1-5}$alkyl-CO$_2$R$^8$ or —C$_{1-6}$alkyl-CONR$^6$R$^7$; and R$^5$ is hydrogen or C$_{1-6}$ alkyl.

3. The compound of claim 2 or a pharmaceutically acceptable salt thereof wherein R$^1$ and R$^2$ are hydrogen, R$^3$ is methyl, R$^4$ is C$_{1-6}$alkyl, hydroxy-C$_{1-6}$alkyl, di(C$_{1-3}$alkyl)amino, 2-furfuryl, or C$_{1-3}$alkoxycarbonylethyl and R$^5$ is hydrogen.

4. The compound of claim 3, or a pharmaceutically acceptable salt thereof wherein Ar is benzo[b]furo-, R$^3$ is CH$_3$, and R$^4$ is —CH$_2$CH$_3$, —N(CH$_3$)$_2$, —CH$_2$CH$_2$OR or —CH$_2$CH$_2$CH$_2$OR wherein R$^5$ is hydrogen or methyl.

5. The compound of claim 4 which is:
(a) (2R,12bS)-N-(1,3,4,6,7,12b-hexahydro-2H-benzo[b]furo[2,3-a]quinolizin-2-yl)-N-methyl-2-hydroxyethanesulfonamide;
(b) (2RS,12bSR)-N-(1,3,4,6,7,12b-hexahydro-2H-benzo-[b]furo[2,3-a]quinolizin-2-yl)-N-methyl-3-hydroxypropanesulfonamide;
(c) (2R,12bS)-N-(1,3,4,6,7,12b-hexahydro-2H-benzo[b]Furo[2,3-a]quinolizin-2-yl)-N-methyl-methanesulfonamide;
(d) (2R,12bS)-N-(1,3,4,6,7,12b-hexahydro-2H-benzo[b]furo[2,3-a]quinolizin-2-yl)-N,N',N'-trimethylsulfamide; or
(e) (2RS,12bSR)-N-(1,3,4,6,7,12b-hexahydro-2H-benzo[b]thieno[2,3-a]quinolizin-2-yl)-N-methyl-methanesulfonamide; or a pharmaceutically acceptable salt thereof.

6. The compound of claim 1, wherein X is —SO$_2$—; R$^4$ is C$_{1-3}$alkyl, phenyl, or 2-furyl; R$^3$ is C$_{1-3}$ alkyl substituted with

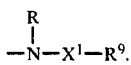

7. The compound of claim 6, wherein $X^1$ is $-SO_2-$.
8. The compound of claim 6, wherein $X^1$ is

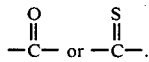

9. The compound of claim 6, wherein $R^4$ and $R^9$ are $C_{1-3}$ alkyl, and R is hydrogen.

10. A pharmaceutical composition having $\alpha_2$-adrenoceptor antagonist activity comprising a pharmaceutically acceptable carrier and an effective $\alpha_2$-adrenoceptor antagonist amount of a compound of structural formula:

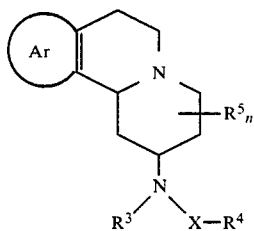

or a pharmaceutically acceptable salt thereof, wherein Ar, $R^3$, X, $R^5$, and $R^4$ are as defined in claim 1.

11. The composition of claim 10 wherein Ar is $R^1,R^2$benzo[b]furo- or $R^1,R^2$-benzo[b]thieno-; $R^1$ and $R^2$ are hydrogen or halo; $R^3$ is $C_{1-6}$alkyl, X is $-SO_2-$ and $R^4$ is $C_{1-6}$alkyl, di($C_{1-3}$alkyl) amino, halo-$C_{1-6}$alkyl, hydroxy$C_{1-6}$alkyl, $C_{2-5}$alkenyl, $C_{6-10}$carbocyclic aryl, 5 or 6-membered heterocycle, $-CO_2R^8$, $-C_{1-5}$alkyl$-CO_2R^8$ or $-C_{1-6}$alkyl-$CONR^6R^7$; and $R^5$ is hydrogen or $C_{1-6}$ alkyl.

12. The composition of claim 11 wherein $R^1$ and $R^2$ are hydrogen, $R^3$ is methyl, $R^4$ is $C_{1-6}$alkyl, hydroxy-$C_{1-6}$alkyl, di($C_{1-3}$alkyl)amino, 2-furfuryl, or $C_{1-3}$ alkoxycarbonylethyl and $R^5$ is hydrogen.

13. The composition of claim 12, wherein Ar is benzo[b]furo-, $R^3$ is $-CH_3$, X is $-SO_2$, and $R^4$ is $-CH_2CH_3$, $-N(CH_3)_2S-CH_2CH_2OR$ or $-CH_2CH_2CH_2OR$ wherein $R^5$ hydrogen or methyl.

14. The pharmaceutical composition of claim 10 wherein the compound is:
(a) (2R,12bS)-N-(1,3,4,6,7,12b-hexahydro-2H-benzo[b-]furo[2,3-a]quinolizin-2-yl)-N-methyl-2-hydroxyethanesulfonamide;
(b) (2RS,12bSR)-N-(1,3,4,6,7,12b-hexahydro-2H-benzo-[b]furo[2,3-a]quinolizin-2-yl)-N-methyl-3-hydroxypropanesulfonamide;
(c) (2R,12bS)-N-(1,3,4,6,7,12b-hexahydro-2H-benzo[b-]furo[2,3-a]quinolizin-2-yl)-N-methyl-methanesulfonamide;
(d) (2R,12bS)-N-(1,3,4,6,7,12b-hexahydro-2H-benzo[b-]furo[2,3-a]quinolizin-2-yl)-N,N',N'-trimethylsulfamide; or
(e) (2RS,12bSR)-N-(1,3,4,6,7,12b-hexahydro-2H-benzo[b]thieno[2,3-a]quinolizin-2-yl)-N-methyl-methanesulfonamide; or a pharmaceutically acceptable salt thereof.

15. The composition of claim 10 wherein X is $-SO_2-$; $R^4$ is $C_{1-3}$alkyl, phenyl, or 2-furyl; and $R^3$ is $C_{1-3}$ alkyl substituted with

16. The composition of claim 15 wherein $X^1$ is $-SO_2-$.
17. The composition of claim 15 wherein

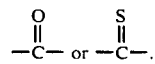

18. The composition of claim 15 wherein $R^4$ and $R^9$ are $C_{1-3}$ alkyl and R is hydrogen.

19. A method of antagonizing $\alpha_2$-adrenoceptors which comprises administering to a patient in need of such treatment an effective $\alpha_2$-adrenoceptor antagonist amount of a compound of structural formula:

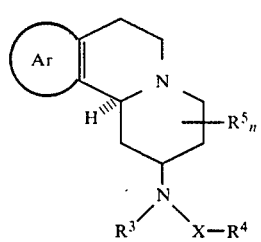

or a pharmaceutically acceptable salt thereof wherein Ar, $R^3$, X, $R^4$, and $R^5$ are as defined in claim 1.

20. The method of claim 19 wherein Ar is $R^1,R^2$-benzo[b]furo or $R^1$, $R^2$-benzo[b]thieno; $R^1$ and $R^2$ are hydrogen or halo; $R^3$ is $C_{1-6}$alkyl; X is $-SO_2-$ and $R^4$ is $C_{1-6}$alkyl di($C_{1-3}$alkyl)amino, halo-$C_{1-6}$hydroxy$C_{1-6}$alkyl, $C_{2-5}$alkenyl, $C_{6-10}$-carbocyclic aryl, 5 or 6-membered heterocycle, $-CO_2R^8$, $-C_{1-5}CO_2R^8$ or $C_{1-6}$alkyl-$CONR^6R^7$; and $R^5$ is hydrogen or $C_{1-6}$ alkyl.

21. The method of claim 20 wherein $R^1$ and $R^2$ are hydrogen, $R^3$ is methyl, Rphu 4 is $C_{1-6}$alkyl, hydroxy-$C_{1-6}$alkyl, di($C_{1-3}$alkyl)amino, 2-furfuryl, or $C_{1-3}$alkoxycarbonylethyl and $R^5$ hydrogen.

22. The method of claim 21 wherein Ar is benzo[b-]furo-, $R_3$ is $-CH_3$, X is $-SO_2-$, and $R^4$ is $-CH_2CH_3$, $-N(CH_3)_2$, $-CH_2CH_2OR$ or $-CH_2CH_2CH_2OR$ wherein $R^5$ is hydrogen or methyl.

23. The method of claim 22 wherein the compound is:
(a) (2R,12bS)-N-(1,3,4,6,7,12b-hexahydro-2H-benzo[b-]furo[2,3-a]quinolizin-2-yl)-N-methyl-2-hydroxyethanesulfonamide;
(b) (2RS,12bSR)-N-(1,3,4,6,7,12b-hexahydro-2H-benzo[b]furo[2,3-a]quinolizin-2-yl)-N-methyl-3-hydroxypropanesulfonamide;
(c) (2R,12bS)-N-(1,3,4,6,7,12b-hexahydro-2H-benzo[b-]furo[2,3-a]quinolizin-2-yl)-N-methyl-methanesulfonamide;
(d) (2R,12bS)-N-(1,3,4,6,7,12b-hexahydro-2H-benzo-[b]furo[2,3-a]quinolizin-2-yl)-N,N',N'-trimethylsulfamide; or
(e) (2RS,12bSR)-N-(1,3,4,6,7,12b-hexahydro-2H-benzo[b]thieno[2,3-a]quinolizin-2-yl)-N-methyl-methanesulfonamide; or a pharmaceutically acceptable salt thereof.

24. The method of claim 19, wherein X is $-SO_2-$; $R^4$ is $C_{1-3}$alkyl, phenyl, or 2-furyl; and $R^3$ is $C_{1-3}$alkyl substituted with

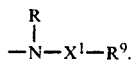

25. The method of claim 24, wherein $X^1$ is $-SO_2-$.
26. The method of claim 24, wherein $X^1$ is

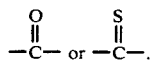

27. The method of claim 24 wherein $R^4$ and $R^9$ are $C_{1-3}$ alkyl and R is hydrogen.

28. The compound of claim 1 or a pharmaceutically acceptable salt thereof where the hydrogen at C-12b and the nitrogen at C-2 are trans, or an enantiomer.

29. The compound of claim 2 or a pharmaceutically acceptable salt thereof where the hydrogen at C-12b and the nitrogen at C-2 are trans, and or an enantiomer.

30. The compound of claim 3 or a pharmaceutically acceptable salt thereof where the hydrogen at C-12b and the nitrogen at C-2 are trans, or an enantiomer.

31. The compound of claim 4 or a pharmaceutically acceptable salt thereof where the hydrogen at C-12b and the nitrogen at C-2 are trans, or an enantiomer.

32. The compound of claim 6 or a pharmaceutically acceptable salt thereof wherein the hydrogen, at C-12b and the nitrogen at C-2 are trans or an enantiomer.

33. The compound of claim 7 or a pharmaceutically acceptable salt thereof wherein the hydrogen-at C-12b and the nitrogen at C-2 are trans or an enantiomer.

34. The compound of claim 8 or a pharmaceutically acceptable salt thereof wherein the hydrogen at C-12b and the nitrogen at C-2 are trans or an enantiomer.

35. The compounds of claim 9 or a pharmaceutically acceptable salt thereof wherein the hydrogen at C-12b and the nitrogen at C-2 are trans or an enantiomer.

36. The composition of claim 10 wherein the compound or a pharmaceutically acceptable salt thereof has the hydrogen at C-12b and the nitrogen at C-2 trans oriented or an enantiomer, 37. The composition of claim 11 wherein the compound or a pharmaceutically acceptable salt thereof has the hydrogen at C-12b and the nitrogen at C-2 trans oriented or an enantiomer.

38. The composition of claim 12 wherein the compound or a pharmaceutically acceptable salt thereof has the hydrogen at C-12b and the nitrogen at C-2 trans oriented or an enantiomers.

39. The composition of claim 13 wherein the compound or a pharmaceutically acceptable salt thereof has the hydrogen at C-12b and the nitrogen at C-2 trans oriented or an enantiomer.

40. The composition of claim 15 wherein the compound or pharmaceutically acceptable salt thereof has the hydrogen at C-12b and the nitrogen at C-2 trans oriented or an enantiomer.

41. The composition of claim 16 wherein the compound or pharmaceutically acceptable salt thereof has the hydrogen at C-12b and the nitrogen at C-2 trans oriented or and enantiomer.

42. The composition of claim 17 wherein the compound or pharmaceutically acceptable salt thereof has the hydrogen at C-12b and the nitrogen at C-2 trans oriented or an enantiomer.

43. The composition of claim 18 wherein the compound or pharmaceutically acceptable salt thereof has the hydrogen at C-12b and the nitrogen at C-2 trans oriented or an enantiomer.

44. The method of claim 19 wherein the compound or pharmaceutically acceptable salt thereof has the hydrogen at C-12b and the nitrogen at C-2 trans oriented or an enantiomer.

45. The method of claim 20 wherein the compound or pharmaceutically acceptable salt thereof has the hydrogen at C-12b and the nitrogen at C-2 trans oriented or an enantiomer.

46. The method of claim 21 wherein the compound or pharmaceutically acceptable salt thereof has the hydrogen at C-12b and the nitrogen at C-2 trans oriented or an enantiomer.

47. The method of claim 22 wherein the compound or pharmaceutically acceptable salt thereof has the hydrogen at C-12b and the nitrogen at C-2 trans oriented or an enantiomer.

48. The method of claim 24 wherein the compound or pharmaceutically acceptable salt thereof has the hydrogen at C-12b and the nitrogen at C-2 trans oriented, or an enantiomer.

49. The method of claim 25 wherein the compound or pharmaceutically acceptable salt thereof has the hydrogen at C-12b and the nitrogen at C-2 trans oriented, or an enantiomer.

50. The method of claim 26 wherein the compound or pharmaceutically acceptable salt thereof has the hydrogen at C-12b and the nitrogen at C-2 trans oriented, or an enantiomer.

51. The method of claim 27 wherein the compound or pharmaceutically acceptable salt thereof has the hydrogen at C-12b and the nitrogen at C-2 trans oriented, or an enantiomer.

* * * * *

UNITED STATES PATENT AND TRADEMARK OFFICE
CERTIFICATE OF CORRECTION

PATENT NO. : 4,690,928

DATED : September 1, 1987

INVENTOR(S) : J. R. Huff et al

It is certified that error appears in the above—identified patent and that said Letters Patent is hereby corrected as shown below:

In Claim 4, Column 38, line 47, "$_2$OR or --" should read ----$_2$OR or -CH$_2$CH$_2$CH$_2$OR----. In line 48, "CH$_2$CH$_2$CH$_2$OR" should be deleted.

In Claim 20, Column 40, line 38, "-C$_{1-5}$CO$_2$R$^8$" should read -- -C$_{1-5}$alkylCO$_2$R$^8$----.

In Claim 21, Column 40, line 41, "Rphu4" should read ----R$^4$----.

Signed and Sealed this

Twelfth Day of January, 1988

Attest:

DONALD J. QUIGG

Attesting Officer  Commissioner of Patents and Trademarks